(12) United States Patent
Rupnick et al.

(10) Patent No.: US 6,306,819 B1
(45) Date of Patent: Oct. 23, 2001

(54) METHOD FOR REGULATING SIZE OF VASCULARIZED NORMAL TISSUE

(75) Inventors: Maria Rupnick, Malden; Robert S. Langer, Newton; Judah Folkman, Brookline, all of MA (US)

(73) Assignees: Massachusetts Institute of Technology, Cambridge; Children's Medical Center Corporation, Boston, both of MA (US)

( * ) Notice: Subject to any disclaimer, the term of this patent is extended or adjusted under 35 U.S.C. 154(b) by 0 days.

(21) Appl. No.: 09/183,556

(22) Filed: Oct. 30, 1998

Related U.S. Application Data

(60) Provisional application No. 60/064,445, filed on Oct. 31, 1997.

(51) Int. Cl.[7] .................... A61K 38/00; A61K 38/02; A61K 31/335

(52) U.S. Cl. .................... 514/2; 514/475; 514/450; 514/12

(58) Field of Search ................. 514/2, 12, 450, 514/475

(56) References Cited

U.S. PATENT DOCUMENTS

| | | |
|---|---|---|
| 5,290,807 | 3/1994 | Folkman et al. . |
| 5,639,725 | 6/1997 | O'Reilly et al. . |

OTHER PUBLICATIONS

Pepper et al. Vascular Medicine, 1(4), 259–266, Jan. 1996.*
Pepper et al. Arteriosclerosis, Thrombosis and Vascular Biology, 17 (4), 605–619, Apr. 1997.*
O'Reilly M. Investigational New Drugs, 15, 5–13, Jan. 1997.*
Weintraub, et al., "Long–term weight control: The National Heart, Lung, and Blood Institute funded multimodal intervention study," *Clin pharmacol Ther*, 51:581–585 (1992).

(List continued on next page.)

Primary Examiner—Michael Borin
(74) Attorney, Agent, or Firm—Holland & Knight LLP

(57) ABSTRACT

Angiogenesis inhibitors are administered to patients in an amount effective to regulate normal, non-transformed vascularized tissue size and/or growth by regulating its vascular compartment. Examples of tissues that can be controlled include adipose tissue, intestinal polyps, muscle (including cardiac) tissue, and endometrial tissue. The response of these tissues to the angiogenesis inhibitors is dose-dependent, reversible, and common to a variety of different angiogenesis inhibitors (examples use TNP-470, angiostatin, and endostatin), based on studies in animal models of obesity, intestinal polyps, cardiac hypertrophy, and endometriosis. Initial studies conducted in an adipose tissue model (genetically obese mice and normal control mice) showed that the growth and mass of adipose tissue is under the control of microvascular endothelium. Expansion of adipose tissue was associated with endothelial cell proliferation. Inhibition of angiogenesis led to reduction in adipose tissue mass. Weight gain in animals receiving angiogenesis inhibitors was significantly restricted, in spite of increases in appetite sufficient to cause weight gain in paired-fed mice. Discontinuation of the inhibitor resulted in rapid expansion of the adipose tissue. The effect was dose-dependent, repeatedly reversible, and occurred in response to all of the inhibitors tested. Significant inhibition was also observed in both the intestinal polyp and cardiac hypertrophy animal models, using dosages of two-thirds or less than the dosages used to treat tumors. Preliminary results in an endometriosis model also show a clear trend towards decreased development of endometriosis in animals treated with angiogenesis inhibitors at a dosage of one-third the dosage used to treat tumors. No effect on normal tissue that was not proliferating, other than adipose tissue, was observed.

13 Claims, 8 Drawing Sheets

OTHER PUBLICATIONS

Wolf & Colditz, "Social and economic effects of body weight in the United States," *Am. J. Clin Nutr.* 63:466S–469S (1996).

Wolf & Colditz, "The costs of obesity: the US perspective," *Pharmacoeconomics* 5:34–37 (1994).

Atkinson, et al., "Report on the NIH workshop on pharmacologic treatment of obesity," *Am J Clin Nutr.* 60:153–156 (1994).

Ball, "The sack–'em–up men: an account of the rise and fall of the modern resurrectionists," p. 73, Oliver and Boyd: Edinburgh, London, 1928.

Blackburn, et al., "Medical evaluation and treatment of the obese patient," *Am J. Cardiol.* 60:55G–58G (1987).

Bray, "Health hazards of obesity," *Endocrin Metab Clin North Amer.* 25:907–919 (1996).

Bray, "Use and abuse of appetite–suppressant drugs in the treatment of obesity," *Ann Intern Med.* 119:707–713 (1993).

Brenot, et al., "Primary pulmonary hypertension and fenfluramine use," *Br. Heart J.* 70:537–541 (1993).

Castelott, et al., "Differentiation–dependent stimulation of neovascularization and endothelial cell chemotaxis by 3T3 adipocytes," *Proc Natl Acad Sci USA.* 7:5597–5601 (1982).

Castelott, et al., "Potent stimulation of vascular endothelial cell growth by differentiated 3T3 adipocytes," *Proc Natl Acad Sci USA.* 77:6007–6011 (1982).

Colditz, "Economic costs of obesity," *Am J Clin Nutr.* 55:503S–507S (1992).

Connacher, et al., "Clinical studies with the β–adrenoceptor agonist BRI 26830A," *Am J Clin Nutr.* 55:258S–261S (1992).

Dobson, et al., "1–Butyryl–glycerol: a novel angiogenesis factor secreted by differentiating adipocytes," *Cell* 61:223–230 (1990).

Drent, et al., "First clinical studies with Orlistat: a short review," *Obes Res.* 3(suppl 4):623S–625S) (1995).

Ezzati, et al., "Sample design: third National Health and Nutrition Examination Survey," *Vital health Stat*[2]. 113 (1992).

Form & Auerbach, "$PGE_2$ and angiogenesis," *Proc Soc Exp Biol Med.* 172:214–218 (1983).

Goldstein, et al., "Fluoxetine: a randomized clinical trial in the maintenance of weight loss," *Obes Res.* 2:92–98 (1993).

Goldstein, et al., "Fluoxetine: a randomized clinical trial in the treatment of obesity," *Int J Obes.* 18:129–135 (1994).

Green, "The adipose conversion of 3T3 cells," in: 10th Miami Symposium on Differentiation and Development, (Ahead, et al., ed.)., pp. 13–33, Academic Press: New York (1978).

Greenway, "Surgery for obesity," *Endo Metab Clin N Amer.* 25:1005–1027 (1996).

Guy–Grand, "Clinical studies with d–fenfluramine," *Am J Clin Nutr.* 55:173s–176 (1992).

Guy–Grand, et al., "International trial of long–term dexfenfluramine in obesity," *Lancet* 2:1142–1144 (1989).

Kramer, et al., "Long–term follow–up of behavioral treatment of obesity: Patterns of weight regain among men and women," *Int J Obes.* 13:123–136 (1989).

Kuczmarski, et al. "Increasing prevalence of overweight among US adults: the National Health and Nutrition Examination Surveys. 1960–1991," *JAMA.* 272:205–211 (1994).

Lau, et al., "Paracine interactions in adipose tissue development and growth," *Intern J Obes.* 20 (Suppl 3) S16–S25 (1996).

Lau, et al., "Influence of paracrine factors on preadipocyte replication and differentiation," *Int J Obes.* 14:193–201 (1990).

Lee, et al., "Change in Body Weight and Longevity," *JAMA* 268(15):2045–2049 (1992).

Long, et al., "Weight Loss in Severely Obese Subjects Prevents the Progression of Impaired Glucose Tolerance to Type II Diabetes," *Diabetes Care* 17(5):372–375 (1994).

McGinnis, et al., "Actual causes of death in the United States," *JAMA* 270:2207–2212 (1993).

Meisler, "American health foundation roundtable on healthy weight," *Am J Clin Nutr.* 63:409S–411S (1996).

National Task Force On Obesity, "Long–term Pharmacotherapy in the Management of Obesity," *JAMA* 276(23):1907–1915 (1996).

NIH Conference, "Gastrointestinal Surgery for Severe Obesity," *Ann Intern Med.* 115(12):956–961 (1991).

NIH Technology Assessment Conference Panel, "Methods for Voluntary Weight Loss and Control," *Ann. Intern. Med.* 119(7):764–770 (1993).

Pasquali, et al., "Clinical aspects of ephedrine in the treatment of obesity," *Int J Obes.* 17(suppl 1):S65–S68 (1993).

Pfohl, et al., "Long–term changes of body weight and cardiovascular risk factors after weight reduction with group therapy and dexfenfluramine," *Int J Obes.* 18:391–395 (1994).

Robison, et al., "Obesity, weight loss, and health," *J Amer Diabetic Assoc.* 93:445–449 (1993).

Ryan, et al., "Medicating the obese patient," *Endo Metab Clin N Amer.* 25:989–1004 (1996).

Samagh, et al., "Expression of FGF–9 and v–fos transformation effector–1 in rat preadipocytes," *Obes Res.* 3:370S (1995).

Silverman, et al., "Angiogenic activity of adipose tissue," *Bioch Biophy Res Com.* 153:347–352 (1988).

Smith, "The endocrinology of obesity," *Endo Metab Clin N Amer.* 25:921–942 (1996).

Stoto, et al., "Healthy people 2000: national health promotion and disease prevention objectives," US Department of Health and Human Services: Washington, DC, 1990.

Teichert–Kuliszewski, et al., "Augmented production of heparin–binding mitogenic proteins by preadipocytes from massively obese persons," *J Clin Invest.* 90:1225–1231 (1992).

The Surgeon General's report on nutrition and health. US Department of Health and Human Services Public Health Service: Washington, DC, 1988.

Voelkel, "Drug–induced pulmonary hypertension: must history repeat itself?" *Pul Phar.* 9:67–68 (1996).

Wadden, "Treatment of obesity by moderate and severe caloric restriction: results of clinical research trials," *Ann Intern Med.* 119:688–693 (1993).

Wassermann, "The development of adipose tissue," in: *Handbook of Physiology Vol. 5*(Renold, A. and Cahill G., eds.), pp. 87–100 Am Physiol Soc.: Washington, DC, 1965.

* cited by examiner

METHOD FOR REGULATING SIZE OF VASCULARIZED NORMAL TISSUE

This claims priority to provisional application U.S. Ser. No. 60/064,445 entitled "Method for Treating Obesity" filed Oct. 31, 1997 by Maria Rupnick, Robert Langer, and Judah Folkman.

FIELD OF THE INVENTION

The present invention is directed generally to the field of treatment of obesity and other disorders characterized by proliferation of normal vascularized tissues, by the administration of effective amount of angiogenesis inhibitors.

BACKGROUND OF THE INVENTION

The prevalence of overweight has reached epidemic proportions in most developed countries and carries with it staggering mortality and morbidity statistics. Obesity is a well established risk factor for a number of potentially life-threatening diseases such as atherosclerosis, hypertension, diabetes, stroke, pulmonary embolism, and cancer. (Meisler J., St. Jeor S. 1996. Am J Clin Nutr. 63:409S–411S). (Bray G. 1996. Endocrin Metab Clin North Amer. 25:907–919). Furthermore, it complicates numerous chronic conditions such as respiratory diseases, osteoarthritis, osteoporosis, gall bladder disease, and dyslipidemias. The enormity of this problem is best reflected in the fact that death rates escalate with increasing body weight. More than 50% of all-cause mortality is attributable to obesity-related conditions once the body mass index (BMI) exceeds 30 kg/m2, as seen in 35 million Americans. (Lee L, Paffenbarger R. 1992. JAMA. 268:2045–2049). By contributing to greater than 300,000 deaths per year, obesity ranks second only to tobacco smoking as the most common cause of potentially preventable death. (McGinnis J., Foege W. 1993. MA.270:2207–22 12).

Accompanying the devastating medical consequences of this problem is the severe financial burden placed on the health care system in the United States. The estimated economic impact of obesity and its associated illnesses from medical expenses and loss of income are reported to be in excess of $68 billion/year. (Colditz G. 1992. Am J Clin Nutr. 55:503S–507S). (Wolf A., Colditz G. 1996. Am J. Clin Nutr. 63:466S–469S). (Wolf A., Colditz G. 1994. Pharmacoeconomics. 5:34–37). This does not include the greater than $30 billion per year spent on weight loss foods, products, and programs. (Wolf A., Colditz G. 1994. Pharmacoeconomics. 5:34–37). (Ezzati, et a. 1992. Vital health Stat [2]. 113).

In 1990, the US government responded to the crisis by establishing as a major national health goal the reduction in the prevalence of obesity to (20% of the population by the year 2000. (Public Health Service. Healthy people 2000: national health promotion and disease prevention objectives. 1990. (US Department of Health and Human Services Publication PHS 90-50212.))

In spite of this objective, the prevalence of overweight in the United States has steadily increased, reaching an astounding 33.0% in the most recent National Health and Nutrition Examination Survey (1988–1991). (Kuczmarski, et al. 1994. JAMA. 272:205–211). Furthermore, the mean BMI has also increased over this period by 0.9 kg/m2. This alarming trend has not occurred as the result of lack of effort. On the contrary, an estimated 25% of men, 50% of women, and 44% of adolescents are trying to lose weight at any given time. (Robinson, et al.J Amer Diabetic Assoc. 93:445–449). Rather, the 31% increase in rate and 8% increase in prevalence over the past decade is a testimony of the fact that obesity is notoriously resistant to current interventions. (NIH Technology Assessment Conference Panel. 1993. Ann Intern Med. 119:764–770).

A major reason for the long-term failure of established approaches is their basis on misconceptions and a poor understanding of the mechanisms of obesity. Conventional wisdom maintained that obesity is a self-inflicted disease of gluttony. Comprehensive treatment programs, therefore, focused on behavior modifications to reduce caloric intake and increase physical activity using a myriad of systems. These methods have limited efficacy and are associated with recidivism rates exceeding 95%.

Failure of short-term approaches, together with the recent progress made in elucidating the pathophysiology of obesity, have lead to a reappraisal of pharmacotherapy as a potential long-term, adjuvant treatment. (National Task Force on Obesity. 1996. JAMA. 276:1907–1915). (Ryan, D. 1996. Endo Metab Clin N Amer. 25:989–1004). The premise is that body weight is a physiologically controlled parameter similar to blood pressure and obesity is a chronic disease similar to hypertension. The goal of long-term (perhaps life long) medical therapy would be to facilitate both weight loss and subsequent weight maintenance in conjunction with a healthy diet and exercise. To assess this approach, the long-term efficacy of currently available drugs must be judged against that of non-pharmacological interventions alone. The latter approach yields an average weight loss of 8.5 Kg at 21 weeks of treatment and only maintains 50% of the weight reduction at 4 years in 10–30% of the patients. (Wadden T. 1993. Ann Intern Med. 119:688–693). (Kramer, et al.1989. Int J Obes. 13:123–136). The few studies that have evaluated long-term (greater than 6 months) single-drug (Guy-Gran, et al. 1989. Lancet. 2:1142–1144) (Goldstein, et al. 1994 Int J Obes. 18:129–135) (Goldstein, et al. 1993. Obes Res. 2:92–98) or combination therapy (Weintraub M. 1992. Clin Pharmacol. Ther. 51:581–585) show modest efficacy compared with placebo in the reduction of body weight.

All medications currently used to treat or prevent obesity are directed at the adipocyte compartment of the tissue and work by either decreasing energy availability or increasing energy output. These agents can be placed into three categories based on mechanism. (National Task Force on Obesity. 1996. JAMA. 276:1907–1915).

Reduction of energy intake. This approach is directed at reducing food intake by decreasing appetite or increasing satiety. These 'anorexiant' drugs affect neurotransmitter activity by acting on either the catecholaminergic system (amphetamines, benzphetamine, phendimetrazine, phentermine, mazindol, diethylpropion, and phenylpropanolamine) or the serotonergic system (fenfluramine, dexfenfluramine, fluoxetine, sertraline, and other antidepressant selective serotonin reuptake inhibitors [SSRI]).

Reduction in absorption of nutrients: Drugs in this category block the action of digestive enzymes or absorption of nutrients. An example of this type of drug is orlistat which inhibits gastric and pancreatic lipase activity. (Drent M., van der Veen E. 1995. Obes Res. 3(suppl 4):623S–625S). These medications are experimental in the United States and not available for the treatment of obesity.

Increase in energy expenditure: An increase in energy expenditure may be accomplished by increasing metabolic rate, for example, through changes in sympathetic nervous system tone or uncoupling of oxidative phosphorylation.

Drugs that affect thermogenesis-metabolism include ephedrine alone and in combination with caffeine and/or aspirin, (Passquali R., Casimirri F. 1993 Int J Obes. 17(suppl 1):S65–S68) and BRL 26830A, a (-adrenoceptor agonist. (Connacher, et al. 1992. Am J Clin Nutr. 55:258S–261S). This class of medications is not approved by the FDA for weight control.

Currently, no single drug regimen emerges as superior in either promoting or sustaining weight loss.

Surgical interventions, such as gastric partitioning procedures, jejunoileal bypass, and vagotomy, have also been developed to treat severe obesity. (Greenway F. 1996. Endo Metab Clin N Amer. 25:1005–1027). Although advantageous in the long run, the acute risk benefit ratio has reserved these invasive procedures for morbidly obese patients according to the NIH consensus conference on obesity surgery (BMI greater than 40 kg/m2). (NIH Conference. 1991. Ann Intern Med. 115:956–961). Therefore, this is not an alternative for the majority of overweight patients unless and until they become profoundly obese and are suffering the attendant complications.

There is no medical or surgical treatment for obesity that is directed at the vascular compartment of the tissue.

It is therefore an object of the present invention to provide a treatment to reduce obesity.

It is a further object of the present invention to provide compositions for treatment of obesity.

It is another object of the present invention to provide methods for inhibiting or decreasing overproliferation of other normal, vascularized tissues.

SUMMARY OF THE INVENTION

Angiogenesis inhibitors are administered to patients in an amount effective to regulate normal, non-transformed vascularized tissue size and/or growth by regulating its vascular compartment. Examples of tissues that can be controlled include adipose tissue, intestinal polyps, muscle (including cardiac) tissue, and endometrial tissue. The response of these tissues to the angiogenesis inhibitors is dose-dependent, reversible, and common to a variety of different angiogenesis inhibitors (examples use TNP-470, angiostatin, and endostatin), based on studies in animal models of obesity, intestinal polyps, cardiac hypertrophy, and endometriosis. Initial studies conducted in an adipose tissue model (genetically obese mice and normal control mice) showed that the growth and mass of adipose tissue is under the control of microvascular endothelium. Expansion of adipose tissue was associated with endothelial cell proliferation. Inhibition of angiogenesis led to reduction in adipose tissue mass. Weight gain in animals receiving angiogenesis inhibitors was significantly restricted, in spite of increases in appetite sufficient to cause weight gain in paired-fed mice. Discontinuation of the inhibitor resulted in rapid expasion of the adipose tissue. The effect was dose-dependent, repeatedly reversible, and occurred in response to all of the inhibitors tested. Significant inhibition was also observed in both the intestinal polyp and cardiac hypertrophy animal models, using dosages of two-thirds or less than the dosages used to treat tumors. Preliminary results in an endometriosis model also show a clear trend towards decreased development of endometriosis in animals treated with angiogenesis inhibitors at a dosage of one-third the dosage used to treat tumors. No effect on normal tissue that was not proliferating, other than adipose tissue, was observed.

DETAILED DESCRIPTION OF THE INVENTION

Figure 1A:
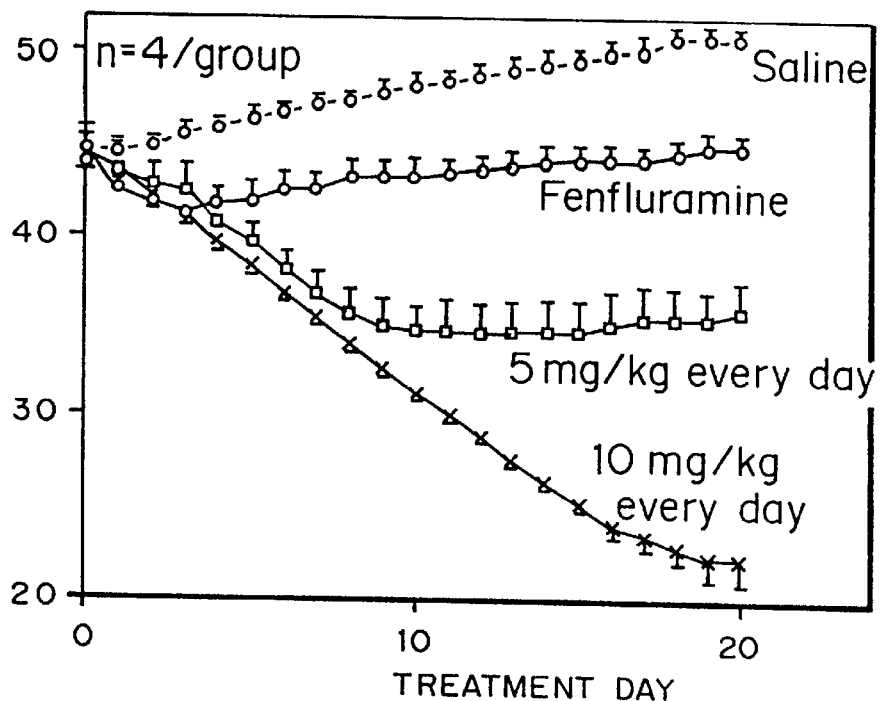
FIG. 1A is a graph of body weight over time (days) in ob/ob mice treated with TNP-470 at either 5 mg/kg daily or 10 mg/kg daily compared to ob/ob mice treated with fenfluramine [40 mg/kg intraperitoneally daily] and saline controls.

Angiogenesis is the process by which new blood vessels are formed. It is essential in reproduction, development, and wound repair, and is highly regulated in these normal events. However, unregulated and persistent angiogenesis also contributes to many disease states such as arthritis, ocular neovascularization, and solid tumor growth. Since 1983, several molecules have been identified that either stimulate or inhibit angiogenesis. These molecules have lead to clinical applications and trials in the areas of diagnostic studies, acceleration of angiogenesis in wound healing, and inhibition of angiogenesis in neoplasia.

Angiogenesis has been extensively studied in the area of solid tumor growth and many of the regulatory factors have been isolated from these tissues. There is substantial evidence that the size and growth of solid tumors is angiogenesis dependent. Simply stated, once a tumor has been initiated, every increase in the tumor cell population must be proceeded by an increase in new capillary formation to supply that tumor. This association has never been made between angiogenesis and 'normal' tissues or organs, such as adipose tissue.

Adipose tissue is a highly vascularized tissue and has been exploited to facilitate wound healing for centuries, (Ball J. 1928. The sack-em-up men: an account of the rise and fall of the modern resurrectionists. Oliver and Boyd, Edinburgh, London. p. 73) primarily due to its ability to promote revascularization of the affected tissue. As a result of this feature, adipose tissue continues to be utilized in surgical procedures involving a variety of tissues in which a vascular supply is vital, such as the intestines, myocardium, and transplanted lung. (Silverman, et al. 1988. Angiogenic activity of adipose tissue. Bioch Biophy Res Com. 153:347–352).

Investigations into the angiogenic aspects of adipose tissue revealed a growth dependence upon the development of a vascular supply. During embryogenesis, vascularization and adipocyte differentiation are tightly coordinated events. Newly formed adipose tissue requires continued angiogenesis for further growth and development. (Wasserman F. 1965. The development of adipose tissue. In: Handbook of Physiology. Vol 5. Renold A., Cahill G., (eds.). Washington, D.C. Am Physiol Soc. PP. 87– 100). Although the mechanisms involved are not yet fully elucidated, bidirectional paracrine interactions between adipocytes and microvascular endothelial cells (EC) are known to play a key regulatory role. (Lau D.,et al. 1996. Intern J Obes. 20 (Suppl 3) S16–S25). This is supported by in vitro studies evaluating the interactions of EC isolated from adipose tissue with 3T3 cells, an adipocyte line that maintains most of the attributes of fat cells in vivo. (Green H. 1978. The adipose conversion of 3T3 cells. In: 10th Miami Symposium on Differentiation and Development. Ahead F., Schultz J., Russe T., Wagner R. (ed.). New York, Academic Press. pp. 13–33). These studies demonstrate that both EC and preadipocytes release mitogenic factors that enhance the proliferation of each other in a cell-specific manner. This symbiotic relationship can be seen in co-cultures, where preadipocytes proliferate in 'islets' around groups of EC. (Lau, et al. 1996. Intern J Obes. 20 (Suppl 3) S16–S25).

Progress has been made in identifying many of the compounds involved. 3T3 adipocytes produce potent factors that stimulate EC proliferation and migration in vitro and angiogenesis in the chick choroiallantoic membrane. (Cystolith, et al. 1982. Proc Natl Acad Sci USA. 77:6007–6011). (Cystolith, et al. 1982. Proc Natl Acad Sci USA. 7:5597–5601). One such compound has been identified as 1-butyryl-glycerol, an angiogenic factor whose levels increase at least 200-fold during adipocyte differentiation. (Dobson, et al. 1990. Cell. 61:223–230). Adipocytes also produce other factors with known angiogenic activity, including PGE1, PGE2, TNF-(, bFGF, and FGF-9. (Form D., Auerbach R. 1983. Proc Soc Exp Biol Med. 172:214–218). (Smith S. 1996. Endo Metab Clin N Amer. 25:921–942). (Teichert-Kuliszewska, et al. 1992. J Clin Invest. 90:1225–1231). (Samagh, et al.1995. Obes Res. 3:370S). Reciprocally, EC isolated from adipose tissue release mitogens into the culture media that stimulate preadipocyte replication in a dose-dependent fashion. (La, et al. 1996. Intern J Obes. 20 (Suppl 3) S16–S25). Partial purification of the EC derived mitogens have revealed several active proteins with molecular weights ranging from 18–67 KDa, some of which may belong to the heparin-binding FGF family. (Lau, et al.1990. Int J Obes. 14:193–201). The complex autocrine/paracrine communications between adipose tissue and EC remains an active area of investigation.

The studies described in the examples provide irrefutable evidence that adipogenesis is dependent on the growth of new blood vessels. By extension and analogous to solid tumor growth—prevention of neovascularization using an anti-angiogenic agents will in turn prevent the growth of adipose tissue. Surprisingly, however, it is also apparent from the examples that angiogenesis can cause weight loss in normal animals, not just in animals in which there is an increased proliferation of adipose tissue. These results provide strong evidence that administration of angiogenesis can be used to regulate size as well as growth of adipose tissue.

Additional studies described in the animals provide further evidence that administration of angiogenesis can be used to regulate the size and/or growth of normal vascularized tissues, without harm to the tissues. As used herein, "normal" tissues refers to tissues which are not cancerous, i.e., transformed, or scar tissue arising from wound healing. As used herein, "vascularized tissue" refers to tissues such as muscle, intestine, adipose tissue, and endometrium, which are normally characterized by a blood supply providing for nutrient and gas exchange throughout the tissue. "Vasculature", in contrast to vascularized tissue, refers to the blood vessels themselves.

I. Compositions for Decreasing Adipose Tissue
A. Compounds Inhibiting Angiogenesis Mechanisms Any anti-angiogenic compound can be used to regulate the size and/or growth of normal vascularized tissue. Preferred exemplary anti-angiogenic compounds include TNP-470, described by U.S. Pat. No. 5,290,807; Angiostatin, described by U.S. Pat. No. 5,639,725; Endostatin, and Thalidomide. Other compounds are known to those skilled in the art. The following list of angiogenic inhibitors was published in Genetic Engineering News, Oct. 1, 1998:

TABLE 1

EXAMPLES OF ANGIOGENIC INHIBITORS AND STIMULATORS IN DEVELOPMENT

| Product Class | Product Name | Company | Product Description | Clinical Indications | Development Stage |
|---|---|---|---|---|---|
| Angiogenic Inhibitors | αvβ3 Antagonist | SmithKline Beecham | Orally active αvβ3 integrain antagonist | Cancer, osteoporosis, RA, restenosis, ocular disease | Preclinical |
| | Angiostatin | EntreMed/Bristol-Meyers Squib | 38 kD fragment of plasminogen | Cancer | Preclinical |
| | Angiostatin- | Genetix | Retroviral delivery of DNA | Cancer | Preclinical |

TABLE 1-continued

EXAMPLES OF ANGIOGENIC INHIBITORS AND STIMULATORS IN DEVELOPMENT

| Product Class | Product Name | Company | Product Description | Clinical Indications | Development Stage |
|---|---|---|---|---|---|
| | endostatin fusion protein | Pharmaceuticals | encoding angiostatin-endostatin fusion protein | | |
| | Anti-Flk/KDR | ImClone Systems | MAb against Flk-1/KDR | Cancer | Preclinical |
| | Anti-VE-Cadherins | ImClone Systems | MAb against endothelial cell junction VE cadherins; prevents assembly of endothelial cells into viable blood vessels | Cancer | Preclinical |
| | Combretastatin A4 | OxiGene | Natural compound derived from bark of a South African tree; disrupts tumor vasculature by binding to tubulin | Solid tumors | Preclinical |
| | Endostatin | EntreMed | 20 kD fragment of collagen XVIII | Cancer | Preclinical |
| | Flt-1 | Merck Research Lab. | Soluble Flt-1 VEGF receptor | Cancer | Preclinical |
| | K5 | Abbott | K5 fragment of human plasminogen | Cancer | Preclinical |
| | 2-methoxy-estradiol | EntreMed | Inducer of endothelial cell apoptosis | Breast cancer | Preclinical |
| | PD-173074 | Parke-Davis | bFGF receptor tyrosine kinase inhibitor | Cancer | Preclinical |
| | RG8803 | Repligen Corp. | Heparin-like carbohydrate; inhibits the binding of VEGF and bFGF to endothelial cell-specific carbohydrate receptors | Solid tumors, and diabetic retinopathy | Preclinical |
| | S-836, SC-68448 | Monsanto USA | $\alpha v\beta 3$ integrin antagonists | Solid tumors | Preclinical |
| | TBC-1635, TBC-2653, TBC-3685 | Texas Biotechnology Corp. | Small molecule antagonist of VEGF Small molecule antagonist of Integrin $\alpha 4\beta 1$ | Diabetic retinopathy, cancer, psoriasis, arthritis | Preclinical |
| | Troponin I | Boston Life Sciences | Recombinant human Troponin 1; thought to act as growth factor receptor antagonist | Cancer and ocular diseases | Preclinical |
| | ANGIOZYME ™ | Ribozyme Pharmaceuticals | Catalytic RNA that specifically cleaves Flt-1 mRNA | Cancer | IND filed |
| | NX 1838 | NeXstar Pharmaceuticals | Oligonucleotide (aptamer) antagonist of VEGF | Age-related macular degeneration | IND filed 7/22/98 |
| | Neoretna Psovascar Neovastat | Aeterna Laboratories | AE-941, a water-soluble extract of shark cartilage; inhibits activity of matrix metalloproteinase II | Macular degeneration Psoriasis Refractory cancers of lung, prostate and breast | Phase I (Canada) Phase I (Canada) Phase I (U.S. & Canada) |
| | EMD-121974 | Merck KGaA | Cyclic peptide antagonist of the $\forall <\exists 5$ integrin | Cancer | Phase I (Germany) |
| | Metastat | CollaGenex Pharmaceuticals | Non-antimicrobial analogue of tetracycline; inhibits activity of matrix metalloproteinase II | Metastatic cancers | Phase I |
| | PI-88 | Progen Industries, Ltd. | Sulfated mannopentasose; acts as a heparan mimetic, prevents release of activated forms of VEGF and bFGF, and, therefore, inhibits angiogenesis. Binds to heparanase, blocks breakdown of vascular membrane and inhibits metastasis | Solid tumors, prevention of restenosis, treatment of asthma and inflammatory bowel disease | Phase I (U.K.) for solid tumors Preclinical for other indications |
| | Squalamine | Magainin Pharmaceuticals | Shark cartilage-derived inhibitor of growth factor-mediated endothelial cell proliferation | Solid tumors | Phase I |
| | Vitaxin | Ixsys | MAb against $\alpha v\beta 3$ integrin; leads to p53-dependent apoptosis of endothelial cells | Cancer | Phase I |
| | SU5416 | Sugen Inc. | Small molecule inhibitor of Flk-1/KDR | Solid tumors, including KS | Phase I/II |
| | Anti-VEGF | Genentech | MAb against VEGF | Solid tumors | Phase II |
| | Thalidomide | EntreMed/Bristol-Meyers Squibb | Small molecule inhibitor of growth factor-mediated endothelial cell preliferation | Brain cancer, KS, metastatic prostate cancer and macular degeneration | Phase II |
| | TNP470 | TAP Holdings, Inc. | Fumagillin analogue | Cancer, arthritis, psoriasis, and ocular disease | Phase II |

TABLE 1-continued

EXAMPLES OF ANGIOGENIC INHIBITORS AND STIMULATORS IN DEVELOPMENT

| Product Class | Product Name | Company | Product Description | Clinical Indications | Development Stage |
|---|---|---|---|---|---|
| | ZD0101 | Zeneca Pharmaceuticals | Polysaccharide endotoxin; stimulates an immune-mediated anti-angiogenic response | Solid tumors | Phase II |
| | Neovastat | Aeterna Laboratories | (see above) | Solid tumors | Phase II/III (Canada) |
| | AG3340 | Agouron Pharmaceuticals | Matrix metalloproteinase inhibitor | Non-SCLC and hormone-refractory prostate cancer | Phase III |
| | Marimastat ™ | British Biotech Inc. | Matrix metalloproteinase inhibitor | Ovarian, small cell and non-small cell lung, pancreatic and gastic cancers and glioblastoma | Phase III |

Another angiogenesis inhibitor that can be used is CM101, a bacterial toxin product, being developed by CarboMedi, Inc., Brentwood, TN.

B. Carriers/routes/means for Administration

Drugs can be administered parenterally or enterally. In the preferred embodiment, drugs are administered orally, in an enteric carrier if necessary to protect the drug during passage through the stomach. Alternative methods of delivery include intravenous, transbuccal or other trans-membrane delivery, and controlled release formulations.

C. Dosages

The anti-angiogenic composition is administered in an amount effective to regulate the size and/or growth of a vascularized tissue. The effective amount will be typically an amount effective to limit tissue proliferation or to decrease tissue size, especially in the case where the tissue is adipose tissue. Compositions as used herein contain an effective amount of angiogenesis inhibitor to treat a patient to achieve the desired regulation in the substantial absence of systemic toxicity.

II. Methods of Treatment

A. Proposed Treatment Schedules

As demonstrated by the examples, the angiogenesis inhibitor is administered in an amount and time period which results in blood levels regulating the size and/or growth of the vascularized tissue to be treated. In the preferred embodiment for the treatment of obesity, patients will receive drug once daily in a dosage effective to decrease the weight to maintenance levels.

B. Types of Patients

The method of treatment has been demonstrated to be applicable to both normal overweight individuals and individuals with genetic defects. The method should also be useful in most cases involving weight gains due to hormonal or metabolic defects or drug side effects. In addition to promoting loss of body fat while maintaining lean body mass and being able to sustain weight loss during chronic administration, other benefits of the treatment include normalization of blood glucose levels in obesity related diabetes, and in the case of some drugs such as TNP-470, reduction of appetite (i.e., as an anorexic agent). These results can be obtained without unwanted side-effects, with no potential for abuse or dependence.

Angiogenesis dependence of normal organ size and growth has implications in the areas where excess or insufficient tissue growth results in clinical sequela, as well as in the field of tissue engineering. The examples demonstrate efficacy in animal models of endometriosis, polyposis, cardiac hypertrophyy, as well as obesity. These results are indicative of efficacy for the treatment of disorders involving increases in size or growth of other types of normal tissue, such as uterine fibroids, prostatic hypertrophy, and amyloidosis. These disorders typically involve patients where increases in size or growth of tissue is not normal, but the tissue is not transformed or of a completely different type of tissue than the tissue of origin, although the location (as in the case of endometriosis) or growth (organ hypertrophy) is abnormal.

III. EXAMPLES

The present invention will be further understood by reference to the following non-limiting examples.

Example 1

Treatment of Genetically Obese Mice with TNP-470

The first series of experiments were performed on ob/ob mice, a strain of mice that develops morbid obesity as a result of a spontaneous mutation in the leptin gene. (Zhang, et al. 1994. Nature. 372:425–432). Animal studies were carried out in the animal facility of Children's Hospital of Boston in accordance with the institutional guidelines. Male ob/ob mice (Jackson Laboratories, Bar Harbor, Me.) with ages ranging from 7 weeks to 6 months and weights ranging from 35 –70 grams were acclimated before experimentation, individually caged, and had free access to water throughout the studies. Animals were anesthetized with inhaled methoxyfluorane (Pitman-Moore, Inc., Mundelein, Ill.) prior to all procedures (shaving, and photography) and were monitored until fully awake. The animals were sacrificed at the end of the experiments by continuous inhalation of methoxyfluorane.

The backs of the mice were shaved to facilitate injections. All injections and measurements were performed between 4–6 p.m. each day. The mice were injected subcutaneously with 5 or 10 mg/kg of TNP-470 (AGM-1470) or saline control using a 30G needle for treatment periods up to 30 days (thus far). The subcutaneous fat was observed to decrease at the site of the TNP-470 injections so the site was varied along the dorsum. For comparison, one group of animals received fenfluramine (40 (:g/kg, intraperitoneally, every day). The weight of each animal and the food remaining were measured each day. One group of animals was paired fed to determine if all or part of the weight loss effect of TNP-470 was the result of appetite suppression. This was done by pairing an untreated mouse with each treated mouse and feeding the untreated mouse the amount of food its treated partner ate the day before.

FIG. 1A demonstrates the weight loss response of mice treated with TNP-470. The treated mice lost weight in a dose dependent fashion. The weight loss in the TNP-470 treated groups was significantly greater than that achieved by fenfluramine at maximal dose. The weight loss of the group receiving 10 mg/kg of TNP continued at an average of 1 gram per day until they reached a lean body mass of approximately 22–24 grams. This weight loss was achievable independent of the weight of the animal at the start of the study. The weights of the animals stabilized at these levels in spite of continued drug administration. The animals receiving a lower dose of TNP-470 stabilized at a higher weight. The animals remained healthy and active throughout the study.

Figure 1B:
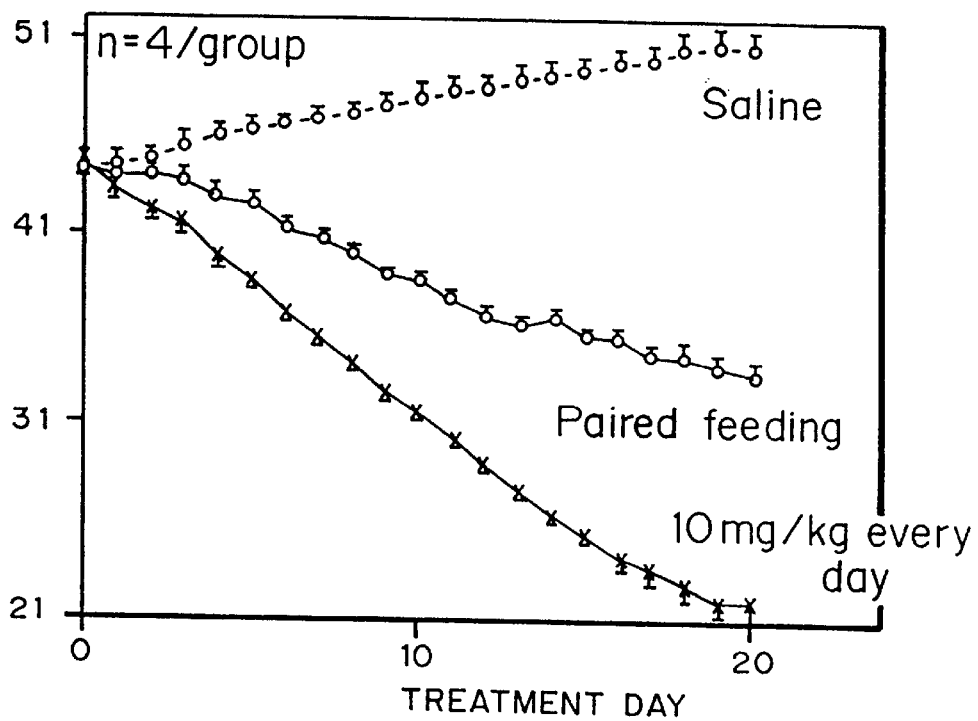
FIG. 1B is a graph of body weight over time (days) in ob/ob mice treated with TNP-470 (10 mg/kg daily) paired feeding [explain], and saline controls.

As shown by FIG. 1B, mice treated with TNP-470 had a decrease in appetite compared with control animals that alone resulted in loss of weight. However, the weight loss resulting from the decrease in food intake was significantly less than that achieved by TNP-470. These results suggest that TNP-470 is acting via two mechanisms to reduce weight—a central appetite suppression and a peripheral angiogenesis inhibition. The appetite suppression effect of TNP-470 has never before been reported.

Example 2

Treatment of Normal Mice to Decrease Fat by Administration of TNP-470.

The paired feeding experiment was repeated using normal mice without the leptin gene mutation that did not develop obesity. In these animals., which began the study relatively closer to their lean body mass, a small weight loss was observed that was similar in the treated and the paired fed groups. This suggests that in a lean animal, in which the angiogenesis occurring in the slowly growing adipose tissue is expected to be limited, the majority of the weight loss achieved with TNP-470 is the result of appetite suppression. These animals also showed no evidence of toxicity.

Samples of adipose tissue were examined histologically for evidence of endothelial cell proliferation indicating new blood vessel formation in both treated and untreated animals using PCNA and Brdu staining methods. There was significantly greater endothelial cell proliferation in the untreated animals compared with those receiving TNP-470. This supports the hypothesis that there is angiogenesis in the adipose tissue of these mice and that it can be inhibited by TNP-470.

In conclusion, TNP470 causes a dose dependent loss of weight in both obese and normal mice to the level of lean body weight as the result of both an appetite suppression and inhibition of angiogenesis independent of the starting weight of the animal. The amount of weight loss achieved with TNP-470 is far superior to that achieved with fenfluramine. These results support the use of angiogenesis inhibition for the treatment of obesity. In addition, an appetite suppression effect of TNP-470 is alsoestablished.

Experimental Procedures

Animal Studies

Animal studies were carried out at Children's Hospital, Boston in accordance with institutional guidelines. Male ob/ob (C57BL/6J) and C57 (C57BL/6J) mice were purchased at 7 weeks of age and acclimated for one week before experimentation (Jackson Laboratories, Bar Harbor, Me.). Mice were housed individually with free access to water and standard chow. Manipulations were performed between 4–6p.m. to minimize disruption of the feeding routine. Animals were anesthetized with inhaled methoxyfluorane (Pitman-Moore, Inc., Mundelein, Ill.) prior to procedures causing discomfort or distress and were monitored until fully awake. The hair was shaved to facilitate injections. TNP-470 was generously provided by Takeda Chemical Industries, Ltd. (Osaka, Japan) and stored dry at 40° C. Solutions were prepared daily in normal saline and administered subcutaneously in rotating sites along the dorsum. Body weight and chow remaining in the feeders were measured daily. Animals were sacrificed by continuous inhalation of $CO_2$.

Dose Response Study

Eight week old, ob/ob mice were treated with 2.5, 5.0, 7.5, or 10 mg/kg/day of TNP-470 for 21 days. A control group received 0.1 ml/day of saline. The group that received 10 mg/kg/day of TNP-470 contained 8 mice, all other groups contained 4 mice each.

Treatment of Morbidly Obese Mice Eight week old ob/ob mice were housed until they completed their rapid growth phase and weighed greater than 60 gm. At approximately 5 months of age (n=6), treatment was initiated with 10 mg/kg/day of TNP-470 and continued for 67 days. An age-matched control group of ob/ob mice (n=6) received 0.1 ml/day of saline.

Long-term Treatment Study

Eight week old (n=6), ob/ob/ mice were treated with 10 mg/kg/day of TNP-470 for 138 days. A control group (n=4) received 0.1 ml/day of saline. Body weights of normal, age-matched C57 mice (n=5) were recorded daily for comparison.

Comparison with Fenfluramine

Eight week old, ob/ob mice were injected intraperitoneally with 40 mg/kg/day of fenfluramine in 0.1 ml of saline for 45 days (n=12). The mice were then evenly divided into 3 groups and were either 1) taken off therapy, 2) continued on fenfluramine, or 3) changed to 10 mg/kg/day of TNP-470 for the remainder of the 168 day study. A control group of ob/ob mice (n=4) received 0.1 ml/day of saline.

Paired Feeding Studies

Eight week old, ob/ob mice with free access to chow were treated with 10 mg/kg/day of TNP-470 (n=4). The chow remaining in the feeder was weighed daily and the amount consumed per day by each mouse was calculated. This amount of food was then fed to a paired mouse in a second untreated group (n=4). The food consumption of a control group of untreated mice with free access to chow was also recorded. The body weights were measured daily. The experiment was repeated with normal, age-matched C57 mice (n=5/group). Paired feeding studies were also performed with angiostatin and endostatin treated mice following this protocol.

Cycled Treatment with TNP-470

Eight week old, ob/ob mice (n=15) were treated with intermittent cycles of 10 mg/kg/day of TNP-470. Mice started at a weight of 45 gm and were treated until they reduced to the body weight of age-matched C57 mice. Treatment was then discontinued and the mice were permitted to gain back to the starting weight of 45 gm. This cycle was repeated twice. Having demonstrated reproducibility here and efficacy in ob/ob mice weighing greater than 60 gm, the treated group was then permitted to gain to an average weight of 59 gm on the third cycle (day 135) before restarting treatment. Subsequently, the mice were cycled between the weights of the ob/ob and C57 control groups. All mice were weighed daily.

Angiostatin and Endostatin Treatment of Obese Mice

Recombinant murine endostatin and angiostatin were produced by Escherichia coli as described by O'Reilly et al, 1994 Cell. 79:315–328; O'Reilly, et al. 1997. Cell. 88:277–285. Eight week old, ob/ob mice (n=3/group) received subcutaneous injections of antiostatin at 20 mg/kg/day or 50 mg/kg twice a day, or endostatin at 50 mg/kg twice a day for 22 days. A control group of ob/ob mice (n=3) received 0.1 ml/day of saline.

Body Composition Assay

The body composition of the mice was assessed using a tritiated water dilution technique (Logsdon, 1972 Radiologic Technology. 44:146–149). Five month old, treated (n=6) and control (n=3) animals from the long-term treatment study with TNP-470 (day 90) and normal age-matched C57 mice (n=3) were used for this study. The mice were fasted for 12 hours with free access to water. They were then gavaged with 200 $\mu$l of tritiated water (100 $\mu$Ci/ml) and remained fasting for an additional 2 hours to allow the tritium to equilibrate within the water compartments. Animals were then anesthetized and placed under a heating lamp for 2 min. to induce tail vasodilation. A 0.5 mm deep incision was made perpendicular to the ventral long axis of the tail, 5 mm from the base using a #10 surgical blade. Care was taken to avoid injuring the central tail artery. A 50 $\mu$l blood sample was collected from the tail veins into serum separator vials and placed on ice. Bleeding was stopped by gentle compression over the incision. Tritiated water specific activity was measured in samples containing 10 $\mu$l plasma and 3 ml of Ecolume scintillation fluid (ICN; Costa Mesa, Calif.) using a Wallac 1409 liquid scintillation counter. Variability between duplicate samples averaged less than 10%. The following formulas were used to calculate the desired parameters.

$$\text{Total Body Water} = \frac{(\text{standard activity}) \times 2{,}000}{(\text{sample activity} - \text{background activity}) \times 1.064} \quad (1)$$

The factor of 1.064 is used to correct for the fact that serum is about 94% water. The factor of 2,000 is the dilution factor needed to calculate the total tritium activity in the dose administered.

$$\text{Lean Body Mass} = \frac{\text{Total Body Water}}{0.73} \quad (2)$$

The factor of 0.73 is the mean percent of total body water found in lean body mass as derived from analysis of cadavers (Widdowson, et. al, 1968).

(3) Fat Mass=Total Body Weight−Lean Body Mass $$\text{Percent Body Fat} = \frac{\text{Fat Mass}}{\text{Total Body Weight}} \times 100 \quad (4)$$

Serum Glucose Measurements

Serum glucose levels of the 9 month old, treated (n=5) and untreated (n=13) ob/ob mice were measured at the end of the weight response study. Blood samples (100 $\mu$l) were collected from the tail veins of anesthetized mice as described above. The serum glucose levels were measured by the clinical chemistry laboratory at Children's Hospital, Boston, and are expressed as mg/dl.

Cell Culture Studies

Bovine capillary endotbelial cells (BCE) were obtained as previously described by Folkman et al, 1979 Proc Natl Acad Sci. USA 76:5217–5221. BCE were plated onto tissue culture plates coated with 1.5% gelatin and cultured in DMEM containing 10% bovine calf serum (BCS), 1% glutamine/antibiotics (GPS), and 3 ng/ml recombinant human basic fibroblast growth factor (bFGF; Scios Nova, Mountainview, Calif.). BCE were maintained at 37° C. in 10% $CO_2$ and were passaged at confluence using a 0.5% trypsin solution. 3T3-L1 cells were obtained from ATCC and maintained according to the accompanying instructions. 3T3-L1 were cultured in DMEM containing 10% BCS without antibiotics and plated onto uncoated tissue culture plates. Cells were passaged when 70% confluent to avoid differentiation in adipocytes using a 0.5% trypsin solution.

Bovine Capillary Endothelial Cell Proliferation Assay

BCE were maintained at confluence for 5 days prior to use in the proliferation assays. The cells were washed with PBS and dispersed in a 0.05% trypsin solution. BCE were resuspended in DMEM containing 10% BCS and 1% GPS (25,000 cells/ml) and plated onto gelatinized 24-well culture plates at a density of 12,500 cells/well (0.5 ml/well). The plates were incubated for 24 hr. The media was replaced with 0.25 ml of assay media (DMEM+5% BCS+1% GPS) containing the test sample at 2× the final concentration. After 30 min. of incubation, 0.25 ml of assay media containing 2 ng/ml of bPGF was added. The wells then contained 0.5 ml of assay media with the test sample at 1× concentration and 1 ng/ml of bFGF. After 72 hr of incubation, cells were dispersed in trypsin, resuspended in Hematall (Fisher Scientific, Pittsburg, Pa.) and counted using a Coulter Counter.

3T3-L1 Cell Proliferation Assay

Subconfluent cultures of 3T3-L1 cells were washed with PBS and dispersed in a 0.05% trypsin solution. The cells were resuspended in DMEM containing 10% BCS (16,000 cells/ml) and plated onto 24-well culture plates at a density of 8,000 cells/well (0.5 ml/well). The plates were incubated for 24 hr. The media was replaced with 0.25 ml of assay media (DMEM+5% BCS) and the test sample at 2× the final concentration. After 30 min. of incubation, 0.25 ml of assay media containing 2 ng/ml of bFGF was added. The wells then contained 0.5 ml of assay media with the test sample at 1× concentration and 1 ng/ml of bFGF. After 72 hrs of incubation, cells were dispersed in trypsin, resuspended in Hematall and counted using a Coulter Counter.

Immunohistochemistry

A double fluorescent labeling technique was used to enable simultaneous identification of proliferating cells (Brdu) and endothelial cells (von Willebrand factor; vWF) in adipose tissue sections. Adipose tissue was fixed for 4 hours in cold Carnoy's fixative and transferred to 100% ethanol. Tissues were embedded in paraffin following standard histological procedures. Sections (5 $\mu$m thick) were permeabilized with 10 $\mu$g/ml proteinase K at 37° C. for 20 n min. and washed with PBS. To label the proliferating cells, sections were incubated with anti-Brdu/nuclease mixture (Brdu Labeling and Detection Kit I; Boehringer Mannheim, Germany) at room temperature for 60 min. and then washed with PBS. Slides were incubated in fluoresceinated horse anti-mouse IgG (Vector; Burlingane, Calif.) at 4° C. overnight. To label the endothelium, sections were blocked with 5% horse serum for 30 min. and then incubated with rabbit antiserum against human von Willebrand factor (DAKO) diluted in 5% goat serum in PBS. Antibody binding was detected by Texas Red-conjugated goat anti-rabbit IgG (Vector Laboratories). Stained sections were preserved with Fluoromount G (Southern Biotechnology Associates, Inc.).

Slides were analyzed using a Zeiss Axiophot fluorescent microscope (Zeiss, Oberkochen, FRG) with blue light at 485 nm for FITC excitation (Brdu) and green light at 510–560 nm for Texas Red excitation (endothelium). Photographs were taken at 40× magnification with Ecktachrome p 1600 film (Eastman Kodak, Rochester, N.Y.). Proliferating endothelium were detectable on the film as yellow cells (green+ red).

Statistical Analysis

A one-tailed Student's t-test was used for comparison of the body weights, percent body fat, and serum glucose levels between the treated and untreated groups. Comparison between the treated and paired fed groups was made using a paired Student's t-test.

Results

Weight Gain in Obese and Non-obese Mice

Both obese (ob/ob) and non-obese (C57) mice used in these studies experienced a period of rapid growth and weight gain during the first few months of life, which slowed as the animals aged. However, the ob/ob mice gained 2–3 fold more weight at much faster rates compared to the age-matched controls. This difference was largely accounted for by the accumulation of excess adipose tissue. In these studies, 8 week old ob/ob mice weighed 44.6±0.7 gm and gained at an average rate of 0.4 gm/day (n+12). For comparison, normal, age-matched C57 mice weighed 23.0±0.6 gm and gained at an average rate of 0.1 gn/day (n=5). Obese mice reached maximum weights of greater than 70 gm at 8–9 months of age, compared to their normal counterparts which reduced maximum weights of greater than 30 gm at 3–4 months of age.

Body Weight Responses of Obese Mice to Angiogenesis Inhibitors

Figure 2:
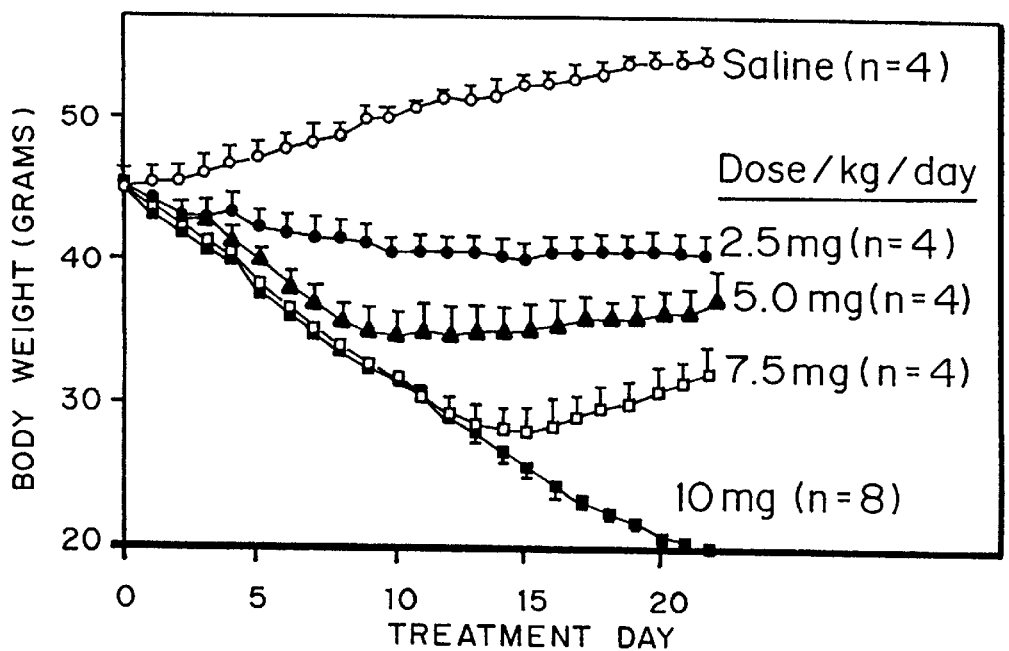
FIG. 2 is a graph of body weight (grams) versus days of treatment, of mice at doses of 2.5, 5.0, 7.5 and 10 mg TNP-470 mg/kg/day versus control. n=4 each group other than 10 mg, which is n=8.

The effect of angiogenesis inhibitors on the ability of ob/ob mice to gain weight was tested. TNP-470, a selective angiogenesis inhibitor, was administered to obese mice at doses of 2.5, 5.0, 7.5, and 10 mg/kg/day for 21 days. Obese mice receiving TNP-470 lost weight at a rate, for a duration, and to an extent that were dose dependent (FIG. 2). Rates of weight loss ranged from 0.5 gm/day at a dose of 2.5 mg/kg/day to a maximum of 1.2 gm/day at doses equal to or greater than 10 mg/kg/day (p <0.00001). For comparison, the maximum rate of weight loss occurring in mice with no caloric intake for 4 days was 1.2 g/day. In spite of continued treatment, the mice leveled or nadired at body weights ranging from 40.5±0.9 gm after 10 days on 2.5 mg/kg/day (p<0.000001). Relative to the average starting weight of 45 gm, this amounted to weight losses of 4–25 gm, depending on the dose of TNP-470. In contrast gm by the conclusion of this study. Relative to the final weights of the control mice, the TNP-470 treated mice weighed 13–34 gm less.

Figure 3:
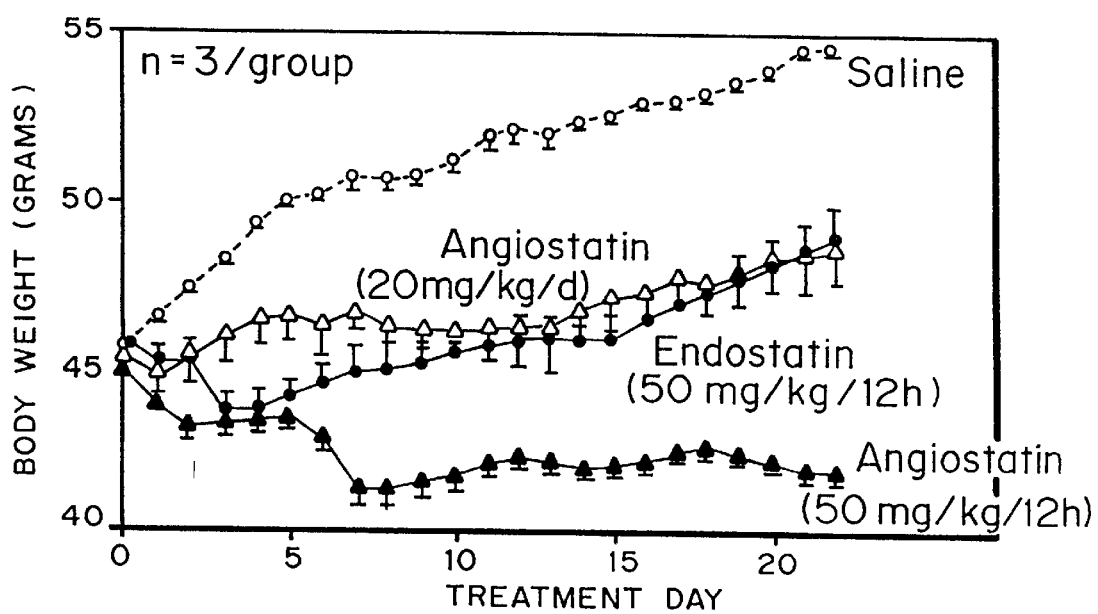
FIG. 3 is a graph of body weight (grams) versus days of treatment, of mice, with angiostatin (20 mg/kg/day), endostatin (50 mg/kg/12 h), and angiostatin (50 mg/kg/12 h) as compared to control treated with saline. n=3 each group.

The body weights of obese mice were also evaluated in response to specific angiogenesis inhibitors. Mice were treated with angiostatin at doses of 20 mg/kg/day or 50 mg/kg twice a day, or endostatin at a dose of 50 mg/kg/day for 21 days (FIG. 3). Control mice gained 0.4 gm/day from an average starting weight of 45 gm, reaching 54.6±0.2 gm by day 22. In contrast, the mice receiving angiogenesis inhibitors gained relatively little or lost weight. The responses to angiostatin were dose dependent. At 20 mg/kg/day, weight gain was restricted to one third that of controls and the mice reached 48.5±1.1 gm by the end of the study (p<0.03). At 50 mg/kg of angiostatin twice a day, the mice reduced to 41.7±0.2 gm and plateaued (p<0.0004). Mice treated with endostatin initially lost about 2 gm, then gradually gained to 48.9±0.8 gm by day 22 (p<0.002). Relative to the final control weights, treated mice weighed 5–13 gm less.

Long-term Treatment with TNP-470

Figure 4A:
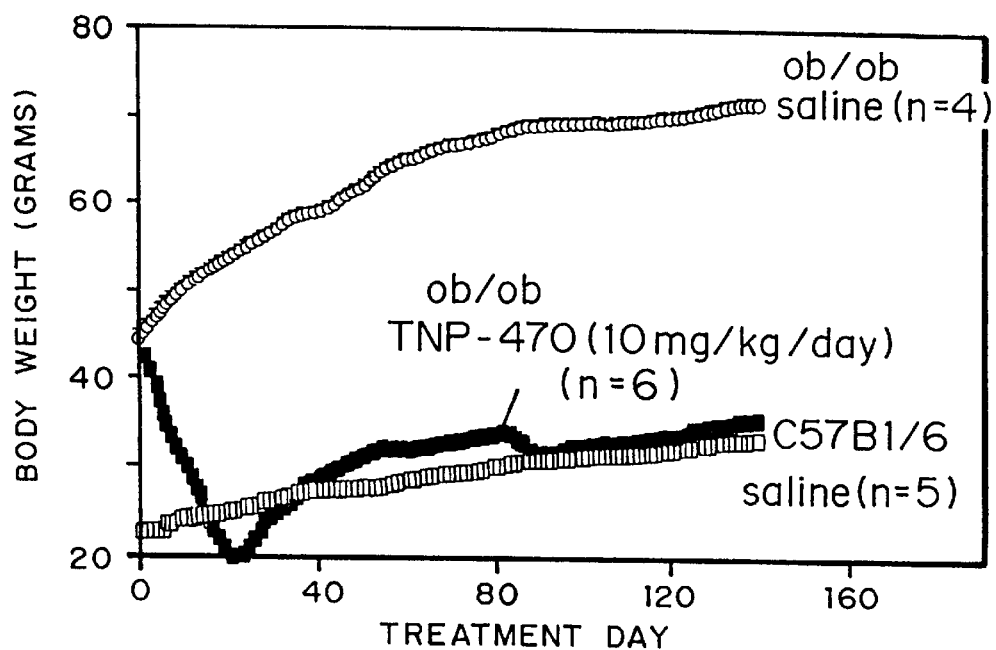
FIG. 4A is a graph of body weight 9grams) versus days of treatment for ob/ob mice treated with 10 mg TNP-470/kg/day (n=6), versus control ob/ob treated with saline (n=4), and normal mice 9C57B 1/6 treated with saline (n=5).

Long-term studies were performed to determine the pattern of body weight response to chronic therapy. The mice were treated with 10 mg/kg/day of TNP-470 for a total of 138 days and the body weights were measured daily (FIG. 4A). Initially, the animals lost weight at an average rate of 1.2 gm/day, reducing to a nadir of 20.2±0.5 gm at day 20. This was followed by a limited period of rapid weight gain. The body weights leveled at approximately 32 gm by day 54 of the study, and then paralleled the growth curve of normal, aged-matched C57 mice.

Animals were fasted for periods totaling 24 hours on days 89–90 of the study to conduct tritiated water dilution experiments. This resulted in a weight loss in all of the groups. However, the treated mice did not regain this lost weight, in spite of returning to an ad librium diet. This is reflected by a dip in the curve followed by re-establishment of the slope at a lower body weight.

At the conclusion of the study, treated mice weighed 34.8±1,1 gm, compared with control ob/ob mice which weighed 71.0±0.9 gm (p<0.00001) and normal, age-matched C57 mice which weighed 33.1±0.7 gm. Treated mice weighed 36 gm less than untreated ob/ob mice.

Body Weight Responses of Obese Mice to TNP-470 at Five Months of Age

As obese mice age, they remain 2–3 times as heavy as normal C57 mice and the rate of weight gain decreases, becoming more analogous to chronic obesity in humans (Chlouverakis and Hojnicki, 1974). To determine whether TNP-470 would be similarly effective under these conditions, ob/ob mice were housed until they completed their rapid growth phase. The mice were 5 months of age and weighed greater than 60 gm at the start of the experiment. Untreated mice gained weight at a rate of 0.1 gm/day reaching 73.0±1.0 gm by the end of the study. In contrast, the treated mice reduced at a rate of 0.2 gm/day to 39.0±1.9 gm by day 40 of treatment and leveled for the duration of the 67 day study (p<0.00001) (FIG. 4). Normal C57 mice weighed approximately 34 gm at this age. Therefore, these older, very obese, and more weight stable animals were equally responsive to TNP-470.

Body Composition of Obese Mice Treated with TNP-470

Figure 4B:
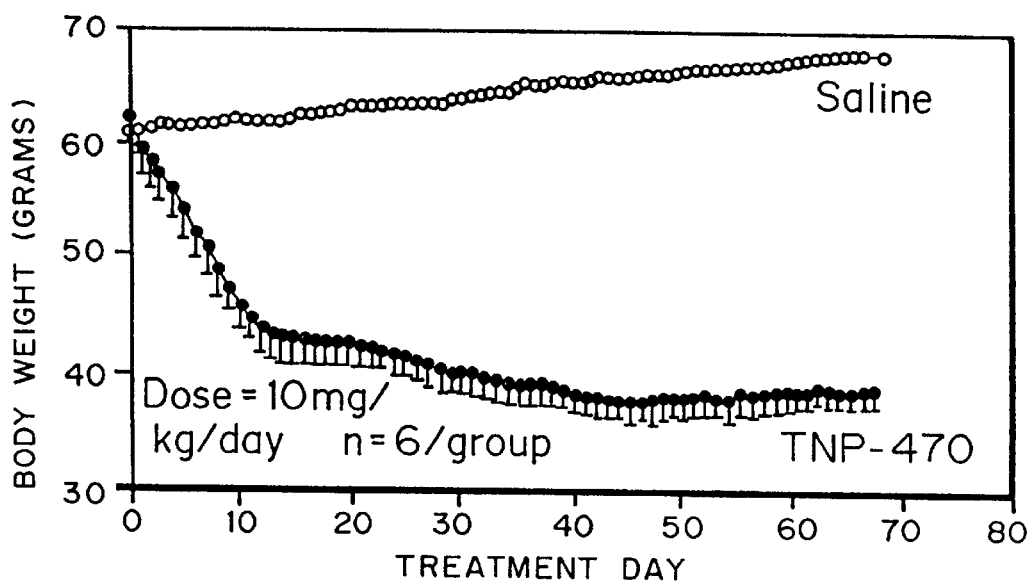
FIG. 4B is a graph of body weight (grams) versus days of treatment for ob/ob mice treated with 10 mg TNP-470kg/day compared with control saline treatment. n=6 for each group.

As the only growing adult organ and site of angiogenesis in normal animals, it was hypothesized that adipose tissue would be selectively susceptible to antiangiogenic therapy. The observation that the body weight of treated animals leveled at the approximate weight of normal, age-matched C57 mice, regardless of starting weight or duration of therapy was consistent with this hypothesis (FIGS. 4A and 4B). A tritiated water dilution technique was used to assess the body composition of the mice and determine if the weight loss was associated with a decrease in percent body fat (Logsdon, 1972). Mice treated with TNP-740 (10 mg/kg/day) for 90 days (FIG. 4A) and age-matched ob/ob and normal, C57B 1/6 mice were used. Weight loss in response to antiangiogenic therapy was associated with a 46% reduction in percent body fat from 35% to 19% (Table 2; p<0.001).

TABLE 2

Percent Body Fat

| Group | Mice/group | Body weight (gm) | Body fat (%) |
|---|---|---|---|
| Untreated ob/ob | 6 | 67.4 ± 0.8 | 35.2 ± 2.2 |
| TNP-470 ob/ob | 6 | 30.6 ± 0.7* | 18.8 ± 1.3** |
| Untreated C57BL/6 | 4 | 28.3 ± 0.7 | 9.2 ± 2.3 |

Treated (TNP-470; 10 mg/kg/day ×90 days) and control ob/ob mice, and age-matched normal C57 mice were fasted and gavaged with a known quantity of tritiated water. The radiolabel was allowed to equilibrate throughout the water compartments of the animal. The amount of label was then measured in a small volume of plasma and the dilution factor was used to determine the total body water, from which the percent body fat was calculated.

\* $p<0.00001$

\*\* $p<0.001$

Serum Glucose Levels of Obese Mice Treated with TNP-470

The morbid obesity in ob/ob mice is associated with the development of insulin resistance and hyperglycemia (Coleman and Hummel, 1973). To determine if the weight loss resulting from antiangiogenic therapy protected against the onset of diabetes, serum glucose levels were measured in ob/ob mice treated with TNP-470 for 115 days and the untreated controls. The untreated mice (73 gm) had an average glucose level of 224±16 mg/dl. In contrast, ob/ob mice treated with TNP-470 (41 gm) had an average glucose level of 158±12.6 mg/dl (p<0.05). This is within the normal range of 62–175 mg/dl reported for this species (Harkness and Wagner, 1995 The biology and medicine of rabbits and rodents. Lea & Febiger Books. Media, Pa. p. 93).

TABLE 2

Serum Glucose Levels

| Group | Mice/group | Body weight (gm) | Body fat (%) |
|---|---|---|---|
| Untreated ob/ob | 11 | 73.0 ± 1.0 | 224 ± 16 |
| TNP-470 ob/ob | 6 | 41.2 ± 1.1* | 158 ± 13** |

Blood samples were drawn from the tail veins of treated (TNP-470; 10 mg/kg/day ×115 days) and control ob/ob mice. Serum glucose levels were measured in serum samples by the Clinical Chemistry Laboratories at Children's Hospital, Boston. *p<0.00001 ** p<0.05

Cycled TNP-470 Treatment of Obese Mice

Figure 4C:
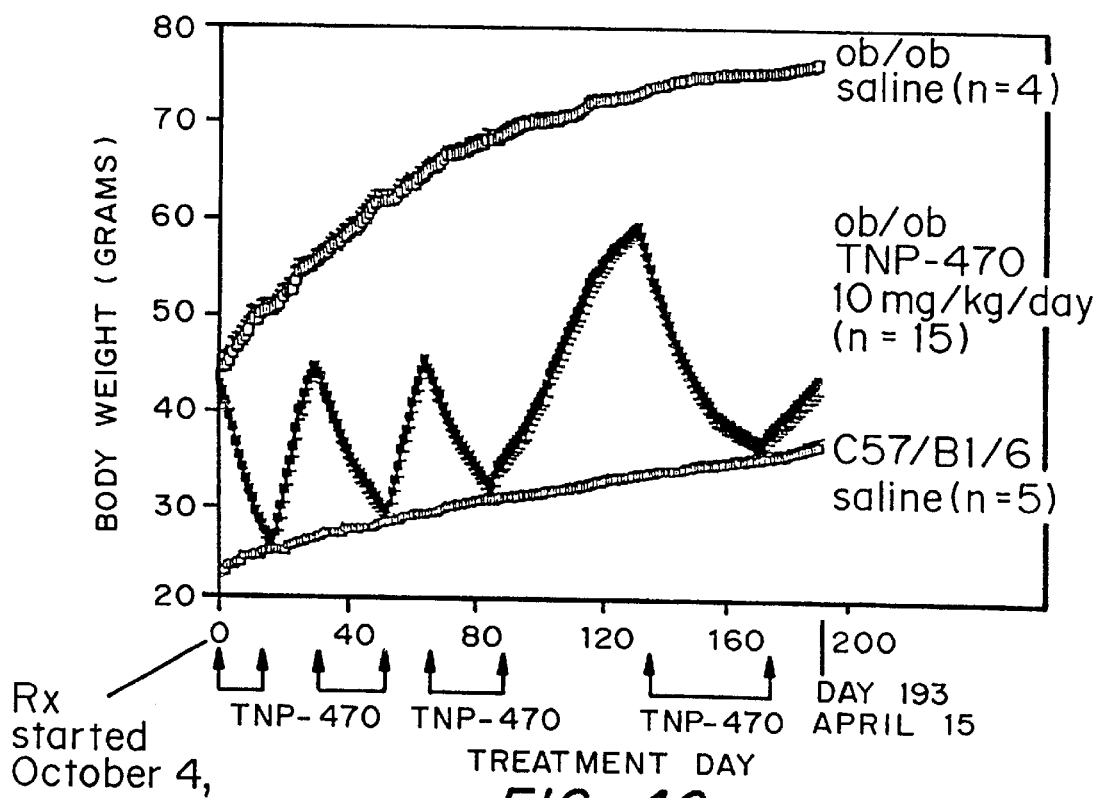
FIG. 4C is a graph of body weight (grams) versus days, for ob/ob animals treated with TNP-470 at a dose of 10 mg/kg/day (n=15), versus normal C57/B1/6 animals treated with saline (n=5) and ob/ob animals treated with saline (n=4).

To demonstrate reversibility and reproducibility of antiangiogenic therapy in this model of normal tissue growth, ob/ob mice were treated with intermittent cycles of TNP-470 at a dose of 10 mg/kg/day (FIG. 4C). Mice started at a weight of 45 gm and were treated until they reduced to the body weight of age-matched C57 mice. Treatment was then discontinued and the mice were permitted to gain back to the starting weight of 45 gm. This cycle was repeated twice. Having demonstrated reproducibility here and efficacy in ob/ob mice weighing greater than 60 gm (FIG. 4B), the treated group was then permitted to gain to approximately 60 gm on the third cycle (day 135) before restarting treatment. This is an ongoing study and the mice are being cycled between the weights of the ob/ob and C57 control groups. The rate of weight gain off therapy was greater than that of controls. Accelerated weight gain has been previously reported in these animals following caloric restriction studies until the normal obese weight is established (Chlouverakis, 1970). The treated mice have similarly and repeatedly reduced while receiving TNP-470 and regained when the drug was discontinued.

Comparison of TNP-470 to Fenfluramine

Figure 5:
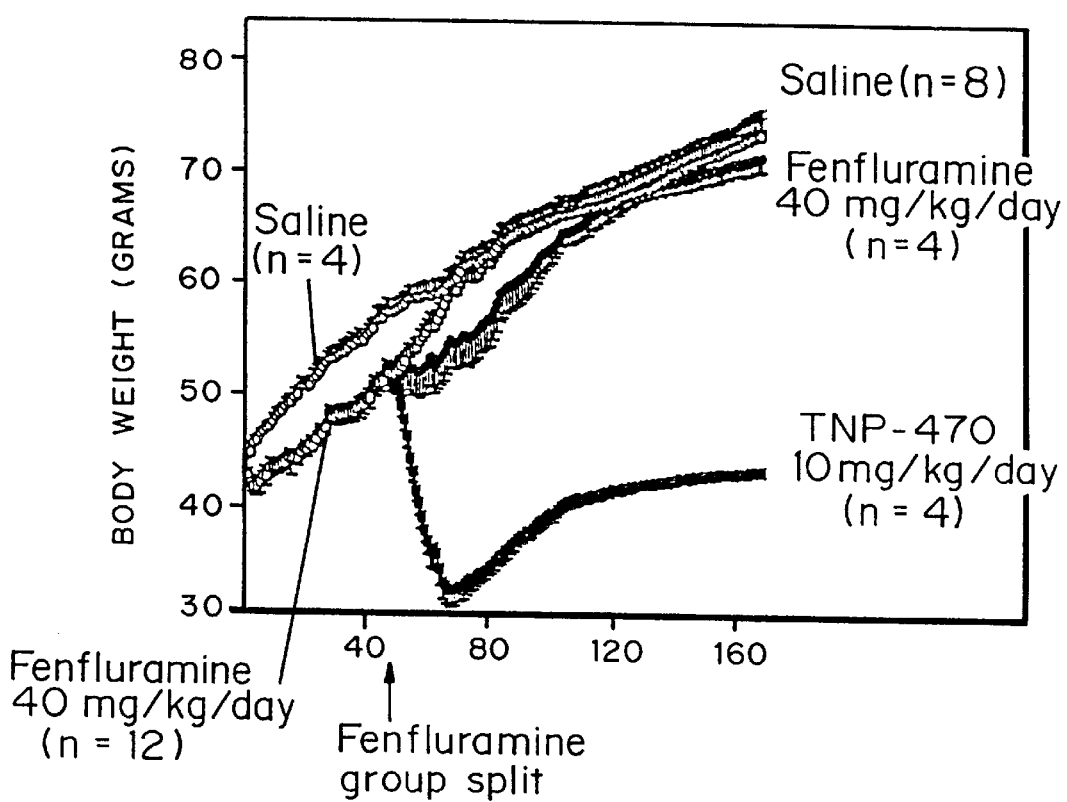
FIG. 5 is a graph of body weight (grams) versus days of treatment of ob/ob animals treated with fenfluramine (40 mg/kg/day, n=4) alone and subsequently with TNP-470 (10 mg/kg/day, n=4).

The weight loss response to TNP-470 was compared to that of fenfluramine, a serotonin uptake inhibitory with anorectic effects (FIG. 5). Obese mice treated with a high therapeutic dose (40 mg/kg/day) of fenfluramine lost 4–5 gm in the first 5 days of therapy (p<0.005). Thereafter, they resumed gaining weight gradually despite continued treatment. On day 45 of the study the fenfluramine treated mice were divided into 3 groups and were either 1) taken off therapy, 2) continued on fenfluramine, or 3) changed to 10 mg/kg/day of TNP-470. By day 94, the control mice weighed 65.8±1.4 gm; mice taken off fenfluramine weighed 65.6+1.4 gm; and mice continued on fenfluramine weighed 62.4+1.9 gm. There was no significant difference between any of these groups. In contrast, substituting TNP-470 for fenfluramine in a subgroup of mice resulted in reduction to the weight of normal C57 mice, 38.5±0.7 gm (p<0.000001). This is further illustrated by the appearance of the mice. Untreated ob/ob mice are not easily distinguishable from those treated with fenfluramine, whereas, mice receiving TNP-470 are the same size as their C57 counterparts.

Tolerance of Long-term Treatment with TNP-470 in Obese Mice

Treatment with TNP-470 has been very well tolerated in doses up to 10 mg/kg/day for periods up to 138 days, thus far. This is approximately ⅓of the life span of the animals. The only adverse effect noted is mild, superficial scaring at the site of repeated injections of the drug. Appetite is moderately suppressed for the first 10–20 days of treatment and then gradually normalizes. The activity level of the treated mice was similar to that of C57 mice and in contrast to control ob/ob mice which became inactive as they gained weight.

In conclusion, these studies have demonstrated that antiangiogenic therapy results in significant weight loss and reduction in body fat in genetically obese mice using three distinct angiogenesis inhibitors. This was further substantiated by the demonstration that inactive preparations of angiostatin and endostatin did not effect body weight. The following series of experiments was directed at determining the mechanism(s). Effects on appetite and on the peripheral tissues are being investigated. The results are summarized below.

Paired Feeding Studies with Obese Mice Treated with Angiogenesis Inhibitors

The effect of appetite on the body weight of TNP-470 treated mice was isolated in paired feeding experiments. The precise amount of chow consumed daily by each treated mouse was fed to a paired mouse in an untreated group FIGS. 6A and 6B). The body weights of the paired mice were used to isolate and measure the effects of appetite changes in the treated animals. Obese mice receiving TNP-470 ate less for approximately the first 18 days of treatment.

Figure 6A:
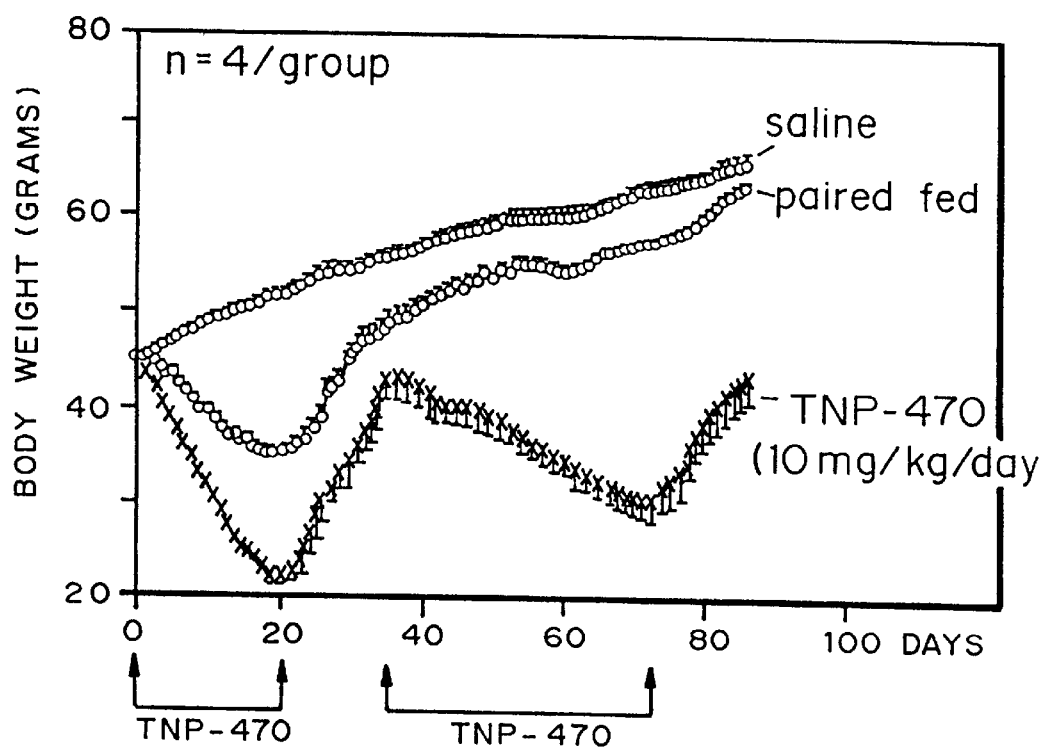
FIGS. 6A and 6B are graphs of body weight (grams) versus day of treatment with TNP-470 (10 mg/kg/day) versus saline controls, in paired feeding experiments.

This accounted for 56% of the initial weight loss. Thereafter, the appetite gradually normalized in spite of continued treatment (up to 138 days), as reflected by a steady gain in the paired mice to near control weights. To determine if the anorexic effect was reversible and reproducible in the same animals, a group of mice was treated with intermittent cycles of TNP-470 and a paired-fed group was used to follow the impact of appetite changes (FIG. 6A). Mice received TNP-470 for 20 days, came off therapy for 15 days, and were then treated a second time for 36 days. The anorexic effect was only present during the initial exposure to TNP-470. During the second cycle of therapy, the treated animals lost weight but maintained their appetite as reflected by the steady increase in the weights of the pair-fed mice. Appetite accounted for only 17% of the weight difference between the treated and untreated mice during the second cycle. The anorexic mechanism is not yet determined.

There was no anorexic effect associated with endostatin or angiostatin at (20 mg/kg/day). Angiostatin at 50 mg/kg twice a day was associated with a small decrease in appetite accounting for less than 20% of the total weight lost.

Paired Feeding Studies with Normal C57 Mice Treated with TNP-470

Figure 6B:
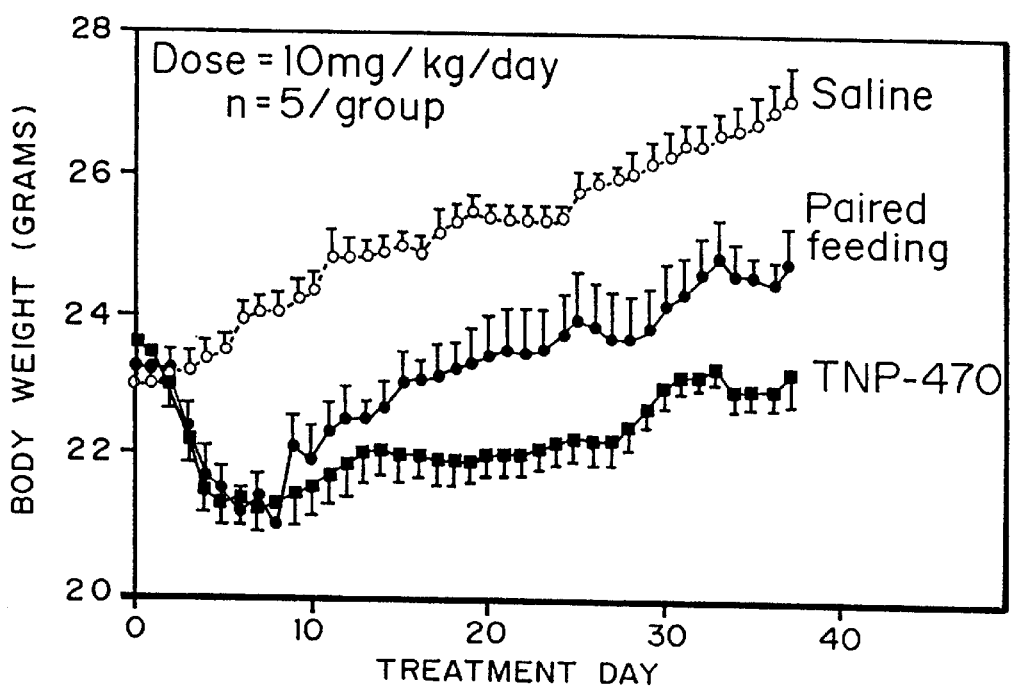
Figure 6C:
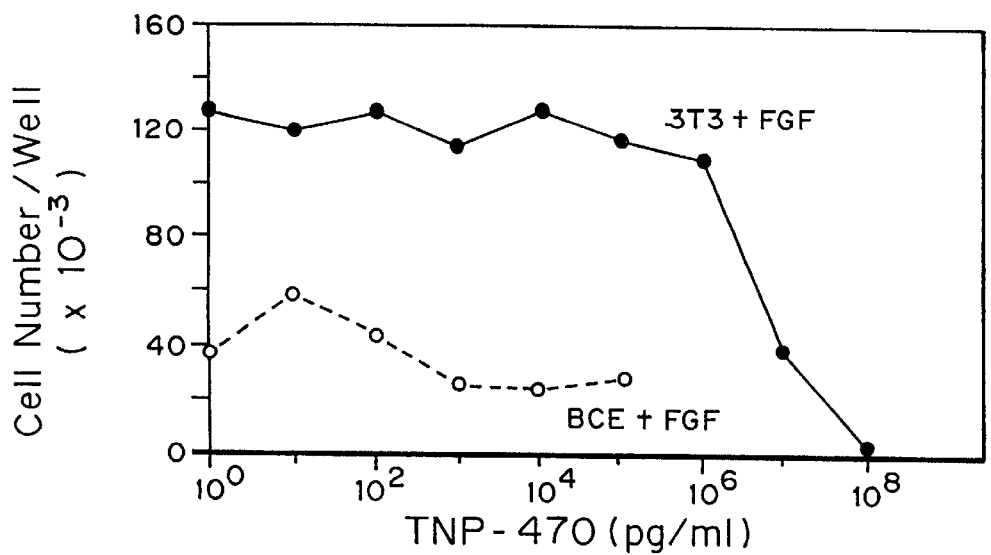
FIG. 6C is a graph of cell number/well ($\times 10^{-3}$) versus TNP-470 (pg/ml) when growth factors, BCE and FGF or 3T3 and FGF, were added to the cells.

Normal C57 mice treated with TNP-470 also lost weight (FIG. 6B). In this case, nearly all of the initial weight loss was attributed to a decrease in appetite, as reflected by the paired-fed mice. The anorexic effect lasted about 8 days, after which the appetite of the treated mice gradually increased and the paired mice gained weight. The treated mice reduced to an average of 85% the control weight ($p<0.00001$). This is significantly less than that seen in the ob/ob mice on the same dose of TNP-470 (56% of control weight). This may reflect the fact that these normal animals have a much lower percent of body fat which appears to be the selective target of this therapy.

The weight loss in the treated animals which not be explained by appetite, is most likely the result of a peripheral effect at the tissue level. This conclusion is further supported by the observation that weight gain of both the ob/ob and C57 mice was restricted by the angiogenesis inhibitors. The treated mice gained relatively little, in spite of an increased food consumption sufficient to cause weight gain in the paired-fed groups.

Endothelial Cell Proliferation in Adipose Tissue of Obese and Normal Mice

To determine whether adipose tissue growth was associated with endothelial cell proliferation, subcutaneous adipose tissue sections from treated and untreated ob/ob mice and normal C57 mice were examined. A double fluorescent staining procedure was used to simultaneously identify both the endothelium and any proliferating cells. The endothelial cell marker, von Willebrand factor (vWF), was stained with a red fluorescent tag and Brdu in proliferating cells was stained with a green fluorescent tag. Proliferating endothelial cells were stained with both tags and appeared yellow.

The adipose tissue of normal C57 mice contained relatively small adipocytes and a high density of endothelial cells as demonstrated by the abundance of red stained cells. Proliferating endothelial cells were also occasionally seen (yellow cells). The adipose tissue of untreated obese mice contained numerous proliferating endothelial cells. The density of endothelial cells was diluted by the large size of the intervening adipocytes in the obese mice. The adipose tissue of treated ob/ob mice contained dilated, tortuous microvessels with a lower percentage of endothelial cells and rare proliferating cells, consistent with inhibition of angiogenesis. Tissue sections from obese mice taken off TNP-470 for one week were also examined. These animals were gaining weight at rates greater than control. The endothelial cell density is notably less than that of normal adipose tissue. However, there is an abundance of proliferating cells. Proliferating endothelial cells (yellow) as well as non-endothelial cells (green) are present. Dilated microvessels, similar to those seen in the treated animals, were also observed.

Endothelial Cell and 3T3-L1 Cells Proliferation in Response to TNP-470

To determine whether TNP-470 may be having a direct effect on preadipocytes, proliferation assays using 3T3-L1 cells were performed. This cell line has most of the attributes of adipose cells in vivo (Green 1978. The adipose conversion of 3T3 cells. In: 10th Miami Symposium on differentiation and development. Ahmad F, Schultz J, Russell T, Werner R (eds). Academic Press, New York. p. 13.). Cells were incubated in a range of TNP-470 concentrations for 72 hours and subsequently counted. Comparisons were made to bovine capillary endothelial cells (BCE). The half-maximal cytostatic inhibition of endothelial cell proliferation was at approximately 100 pg/ml. In contrast, 10 $\mu$g/ml of TNP-470 was required for a similar degree of inhibition in the 3T3-L1 cultures.

Conclusions

These studies demonstrate that an adipose tissue growth and mass is angiogenesis dependent; angiogenesis inhibitors reduce body weight and adipose tissue mass; reduction of body weight with antiangiogenic agents is dose dependent, reversible, and occurs regardless of starting weight; weight reduction was achieved with every angiogenesis inhibitor tested; TNP-470 results in a transient decrease of appetite; long-term treatment with angiogenesis inhibitors is well tolerated; treatment of morbid obesity with angiogenesis inhibitors prevents hyperglycemia.

Example 3

Treatment of Animals with Cardiac Hypertrophy using Angiogenic Inhibitors.

Model

Chronically elevated thyroid hormone levels result in volume overload of the heart leading to eccentric cardiac hypertrophy in both animals and man (Osler W. 1892. The principles and practice of medicine. D. Appelton and Company. New York, pp. 712–714). Myocardial hypertrophy is usually associated with abnormalities of the coronary vascular system and eventual loss of ventricular function (Tomanek and Hovanec, 1981 J Mol Cell Cardiol. 13:471–488; Friberg, 1988 Cardiovasc. Res. 22:329–339.). However, thyroid hormone induced cardiac hypertrophy is unique in that there is frequently enhanced ventricular function and a proliferation of the supporting microvascular system (Tomanek et al, 1998 Circ Res. 82:587–593). It was hypothesize that the growth of cardiac tissue in this model of myocardial hypertrophy may be mediated by the vascular endothelium and could be suppressed with the use of angiogenesis inhibitors. The implications of such a finding relate to the role of the vascular endothelium as a regulator of normal cardiac mass and function.

Methods

Animal studies were carried out at Children's Hospital, Boston in accordance with institutional guidelines. Male C57BL/6J mice were purchased at 6 weeks of age and acclimated for one week before experimentation (Jackson Laboratories, Bar Harbor, Me.). Mice were caged collectively and had free access to water and standard chow. Animals were anesthetized with inhaled methoxyfluorane prior to procedures causing discomfort or distress and were monitored until fully awake. The hair was shaved to facilitate injections. Mice were treated with thyronine (0.2 mg/kg/day, i.p.) for 12 days to induce cardiac hypertrophy. In addition, mice simultaneously received s.c injections of saline or TNP-470 at either 10 mg/kg or 20 mg/kg every other day (n=3/group). Results were compared to controls treated with saline alone (no thyronine). Animals were weighed at the end of the study and sacrificed by cervical dislocation. The hearts were immediately removed and placed in warmed buffer solution while still beating to empty the organ of remaining blood. The ventricles were dissected clean of the great vessels, atria, and connective tissue and the chambers were opened. The tissues were blotted dry and weighed. Ventricular weights were normalized to body weight and presented as percent of body weight.

Results

Figure 7:
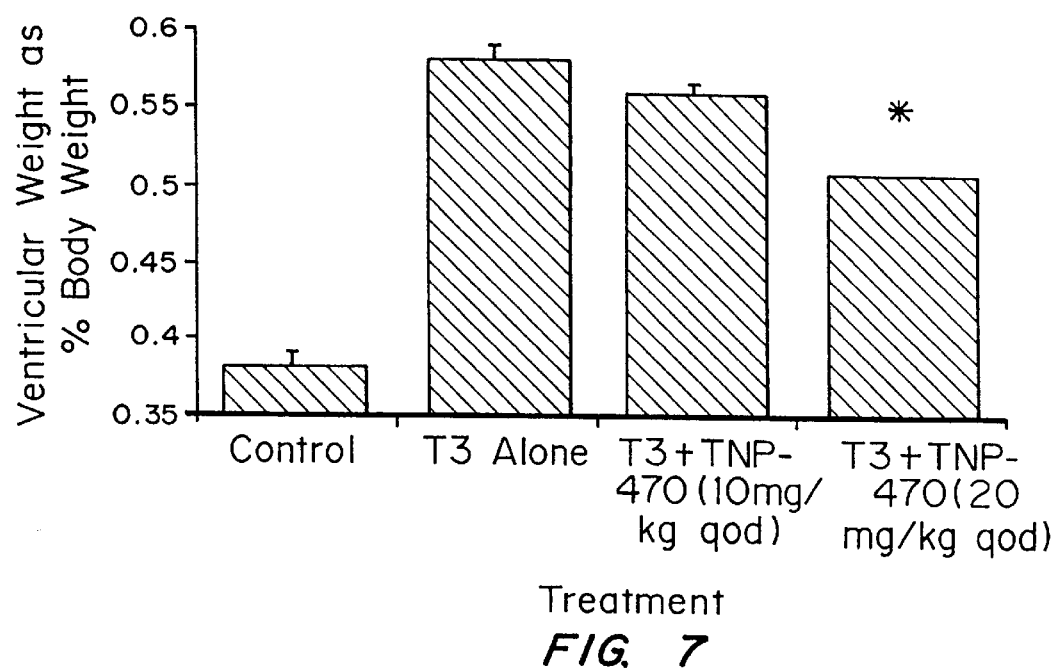
FIG. 7 is a graph of ventricular weight as % body weight of animals with thyronine induced ventricular hypertrophy, treated with T3 (induces hypertrophy), T3 and TNP-470 at 10 mg/kg qod, and T3 and TNP-470 at 20 mg/kg qod.

Thyronine treatment resulted in cardiac hypertrophy, increasing the ventricular weight from 0.38% to 0.58% of body weight. This effect was blunted by TNP-470 in a dose dependent fashion (FIG. 7). At a TNP-470 dose of 20 mg/kg, the ventricular weight achieved with thyronine treatment was significantly less than controls, at 0.51% of body weight ($P<0.05$). Furthermore, these figures may underestimate the effects of TNP-470, given that there was a weight loss of 1–2 gm in the mice receiving TNP-470 during the 12 day study. The decrease in weight results from a decrease in adipose tissue mass. However, the cardiac size of the treated animals is expected to be appropriate for their higher starting weight. Studies to verify this are in progress. The doses tested thus far are 2/3 less than typically used to treat cancer in mice. A greater reduction in hypertrophy is expected with higher doses.

Example 4:

Treatment of Intestinal Polyposis with Angiogenesis Inhibitors

Model

Apc$^{Min}$ mice serve as a model of intestinal adenomatous polyps. Min (multiple intestinal neoplasia) is an ethylnitrosourea (ENU)-induced mutation in the murine Apc (adenomatous polyposis coli) gene (Moser et al, 1990). It is similar to the germline mutations in the APC gene in humans with familial adenomatous polyposis or Gardner Syndrome (Joslyn et al, 1991 Cell. 66:601–613). These are inherited conditions characterized by intestinal polyps that eventually transform into cancer. APC is the most frequently mutated gene in sporadic human colon cancer, as well (Nishisho et al, 1991 Science. 253:665–668).

Heterozygous C57B1/6JMin/+ mice spontaneously develop 30–60 adenomas throughout the intestine during the course of their lifetimes (Moser et al, 1990 Science. 247:322–324). The polyps continue to grow in size, ultimately leading to the death of the animals by about 120 days of age.

It was hypothesized that the growth of these pre-neoplastic lesions is dependent on the vascular endothelium and could be suppressed with the use of angiogenesis inhibitors.

Methods

Animal studies were carried out at Children's Hospital, Boston in accordance with institutional guidelines. Male Min/+ (C57BL/6J) mice were purchased at 6 weeks of age and acclimated for one week before experimentation (Jackson Laboratories, Bar Harbor, Me.). Mice were caged collectively and had free access to water and standard chow. Animals were anesthetized with inhaled methoxyfluorane (Pitman-Moore, Inc., Mundelein, Ill.) prior to procedures causing discomfort or distress and were monitored until fully awake. The hair was shaved to facilitate injection.

TNP-470 was stored dry at 40° C. Solutions were prepared fresh in normal saline and administered subcutaneously in rotating sites along the dorsum. Mice were treated with 10 mg/kg of TNP-470 every other day for 1 or 3 weeks (n=3/group). A control group received 0.1 ml of saline every other day (n=3).

Chow was withheld for 12 hours prior to the termination of each study to clear the intestinal tract. Animals were sacrificed by continuous inhalation of $CO_2$. The entire intestinal tract was removed and flushed with phosphate buffered saline. The intestine was opened longitudinally and the luminal surface was examined for the number, size, and location of polyps using a dissecting microscope (magnification 18×). Tissue samples were fixed in buffered formalyn and embedded in paraffin. Sections were stained with H&E for histologic evaluation.

Results

Figure 8A:
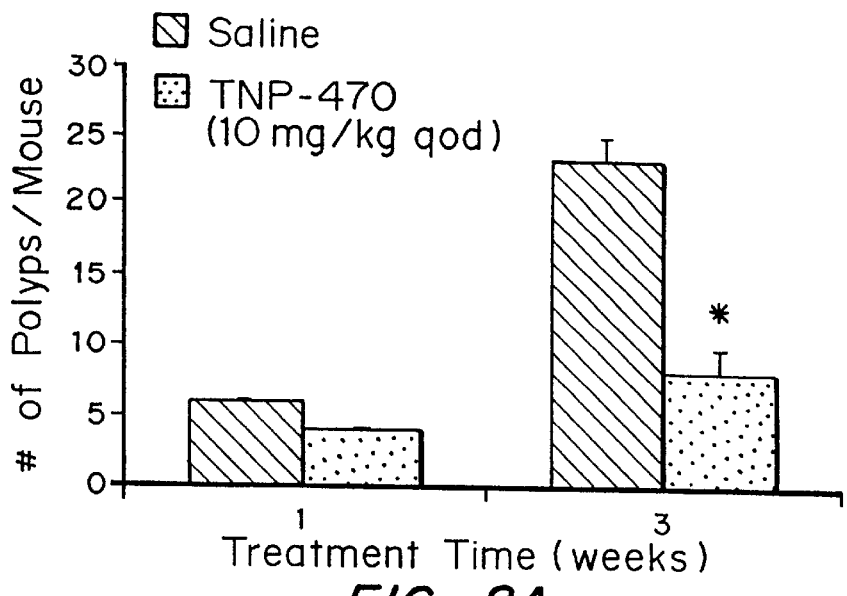
FIG. 8A is a graph of the number of polyps in Min/+ mice, saline controls versus animals treated with TNP-470 at a dose of 10 mg/kg qod, after one and three weeks.
Figure 8B:
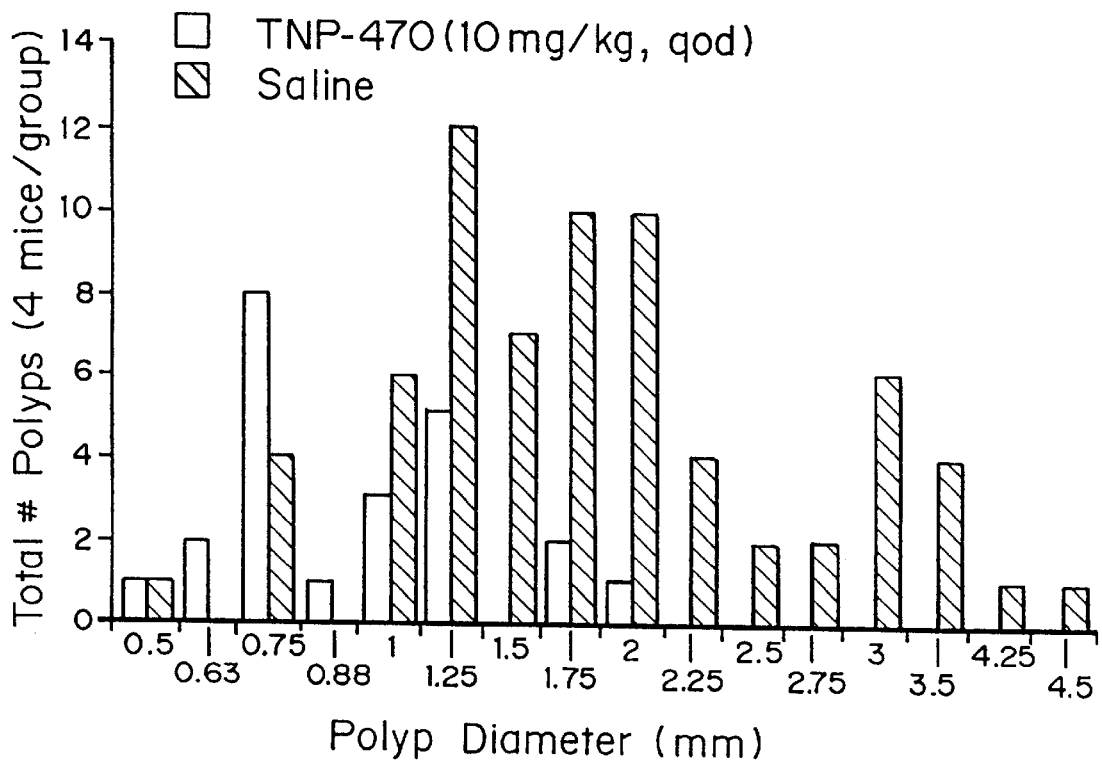
FIG. 8B is a graph of the size distribution of polyp size in Min/+ mice, graphed as total number of polyps of each size (diameter in mm) for animals treated with TNP-470 at 10 mg/kg qod, versus saline controls.

The number and size of intestinal polyps was significantly reduced in Min/+ mice treated with an angiogenesis inhibitor. Following 3 weeks of treatment, control mice had 23±1.5 polyps, while mice treated with TNP-470 had 8±1.7 polyps (FIG. 8A). This is a reduction of 66% ($p<0.05$). The diameter of the polyps in the control mice averaged 1.90±0.86 mm (range 0.075 to 0.425 mm) (FIG. 8B). In contrast, the diameter of the polyps in the treated mice averaged 1.02±0.40 mm (range 0.05–0.175 mm).

Histologic examination of polyps from the control mice demonstrated marked cellular dysplasia and numerous cavernous vessels. Lesions were polyploid, extending from the mucosa into the lumen and occasionally outward through the visceral surface. In contrast, polyps from the treated mice retained morphologic similarity with the surrounding mucosa, with fewer dysplastic cells and fewer, smaller vessels.

Conclusion

The occurrence, growth, and possibly transformation of intestinal adenomatous polyps is angiogenesis dependent and regulated by the vascular endothelium.

Example 5

Treatment of Animals with Endometriosis.Using Angiogenic Inhibitors

Model

Up to 50% of all menstruating women may be afflicted with endometriosis (Williams and Pratt, 1977 Am J Obstet Gynecol. 129:245.). Human endometriosis can be surgically mimicked in a rodent model (Cummings and Metcalf, 1996 PSEBM. 212:332). Studies were designed to test whether the growth of these tissue implants is dependent on the vascular endothelium and could be suppressed with the use of angiogenesis inhibitors.

Methods

Animal studies were carried out at Children's Hospital, Boston, Mass., in accordance with institutional guidelines. Female (B6C3F1) mice were purchased at 8 weeks of age and acclimated for one week before experimentation (Jackson Laboratories, Bar Harbor, Me.). Mice were caged collectively and had free access to water and standard chow. Animals were anesthetized with inhaled methoxyfluorane (Pitman-Moore, Inc., Mundelein, Ill.) prior to procedures causing discomfort or distress and were monitored until fully awake. The hair was shaved to facilitate injections.

TNP-470 was stored dry at 40° C. Solutions were prepared fresh in normal saline and administered subcutaneously in rotating sites along the dorsum. Mice were treated with 10 mg/kg of TNP-470 every other day for 3 weeks (n=4/group). A control group received 0.1 ml of saline every other day Using aseptic technique, mice were anesthetized and the abdominal hair was shaved. A midventral incision was made and the left uterine horn was exposed and ligated at both ends. The uterine horn was excised, placed in warmed media (Ham's F12) and opened longitudinally. Pieces of tissue were cut 2 mm in diameter using a dermal punch biopsy. The tissue pieces were position on the intestinal mesentary (4 pieces/animal). Implants were held in place with a fibrin glue preparation. The abdominal incision was closed and the mice were permitted to recover for 48 hours. Thereafter, the mice were divided into two groups of 4 mice each. The control group was treated with saline. The treatment group received TNP-470 (10 mg/kg, every other day). The animals were sacrificed by continuous inhalation of $CO_2$ three weeks following surgery. The peritoneal cavity was examined for endometrial tissue. The tissue was counted and the diameters were measured in the x and y dimensions using calipers and averaged.

Results

Figure 9:
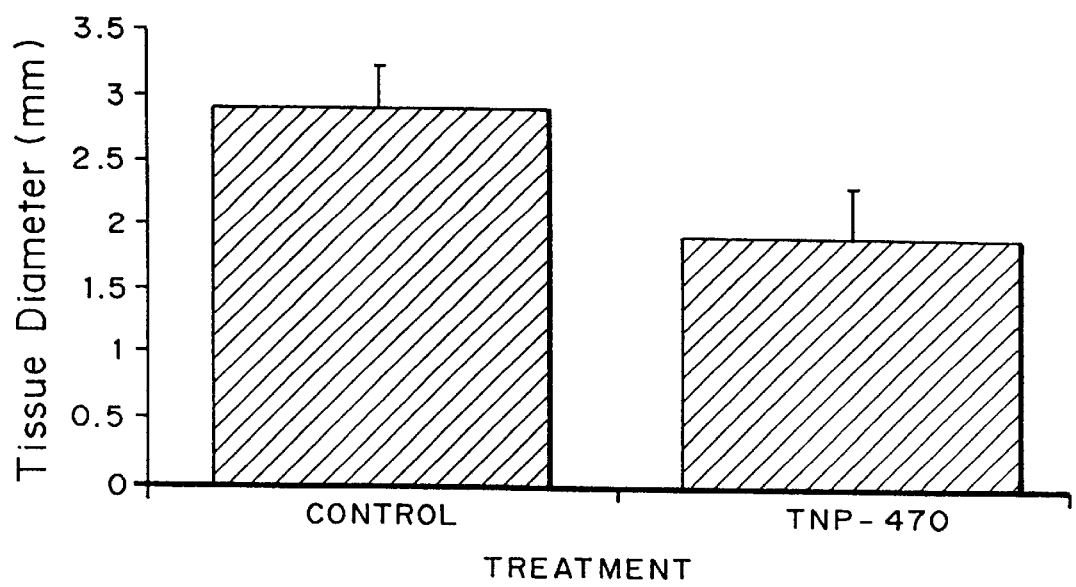
FIG. 9 is a graph of tissue diameter (mm) in an animal model of endometriosis for control animals and animals treated with TNP-470.

The size of the endometrial tissue was reduced in mice treated with an angiogenesis inhibitor. Following 3 weeks of treatment, control mice endometrial tissue measured 2.9±0.4 mm, while mice treated with TNP-470 endometrial tissue measured 1.9±0.5 mm, as shown by FIG. 9. The number of tissue implants was similar between the two groups.

Conclusion

The data indicates that the growth of endometrial tissue implanted into the abdominal cavity is suppressed by angiogenesis inhibitors. The dose of TNP-470 used in this pilot study is ⅓ of the established tumor dose.

We claim:

1. A method of decreasing the size and/or growth of tissue selected from the group consisting of adipose tissue, endometrium tissue, benign polyps, hypertrophied cardiac tissue, hypertrophied renal tissue, hypertrophied prostatic tissue and tissue containing amyloid deposits in a human or animal comprising administering an effective amount of angiogenesis inhibitor to the animal to decrease the size or growth of the vascularized normal tissue.

2. The method of claim 1 wherein the inhibitor is a collagenase inhibitor.

3. The method of claim 1 wherein the inhibitor is selected from the group consisting of TNP-470, angiostatin, endostatin, and thalidomide.

4. The method of claim 1 wherein the normal vascularized tissue is adipose tissue.

5. The method of claim 4 wherein the animal or human has a genetic defect resulting in obesity.

6. The method of claim 4 whereby the inhibitor suppresses appetite.

7. The method of claim 6 wherein the inhibitor is TNP-470 administered in an amount effective to suppress appetite.

8. The method of claim 7 wherein the TNP-470 is administered in an amount effective to reduce the vascular supply to adipose tissue.

9. The method of claim 1 wherein the tissue is selected from the group consisting of endometrium tissue, benign polyps, hypertrophied cardiac tissue, hypertrophied prostatic tissue.

10. The method of claim 9 wherein the animal or human has polypsis.

11. The method of claim 9 wherein the animal or human has endometriosis.

12. The method of claim 9 wherein the animal or human has an enlarged prostate.

13. The method of claim 9 wherein the animal or human has cardiac or renal hypertrophy.

* * * * *

UNITED STATES PATENT AND TRADEMARK OFFICE
CERTIFICATE OF CORRECTION

PATENT NO. : 6,306,819 B1  Page 1 of 1
APPLICATION NO. : 09/183556
DATED : October 23, 2001
INVENTOR(S) : Marla Rupnick, Robert S. Langer and Judah Folkman It is certified that error appears in the above-identified patent and that said Letters Patent is hereby corrected as shown below:

Claim 1, column 24, line 2, delete "and/or growth".
Claim 1, column 24, line 2, insert --enlarged normal vascularized normal-- after "of".
Claim 1, column 24, lines 8 and 9, delete "or growth".
Claim 1, column 24, line 9, insert --enlarged normal-- after "the".

Signed and Sealed this

Twenty-seventh Day of November, 2007

JON W. DUDAS
*Director of the United States Patent and Trademark Office*